US009133111B2

(12) United States Patent
Louis et al.

(10) Patent No.: US 9,133,111 B2
(45) Date of Patent: *Sep. 15, 2015

(54) HIGH PURITY DIPHENYL SULFONE, PREPARATION AND USE THEREOF FOR THE PREPARATION OF A POLY(ARYLETHERKETONE)

(71) Applicant: Solvay Advanced Polymers, LLC, Alpharetta, GA (US)

(72) Inventors: Chantal Louis, Alpharetta, GA (US); William Gandy, Alpharetta, GA (US); Edward Ryan, Roswell, GA (US); Geoffrey Scott Underwood, Atlanta, GA (US); Kong Yi, Marietta, GA (US)

(73) Assignee: Solvay Advanced Polymers, L.L.C., Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/246,901

(22) Filed: Apr. 7, 2014

(65) Prior Publication Data

US 2014/0221595 A1    Aug. 7, 2014

Related U.S. Application Data

(63) Continuation of application No. 13/125,508, filed as application No. PCT/EP2009/064007 on Oct. 23, 2009, now Pat. No. 8,710,171.

(60) Provisional application No. 61/140,205, filed on Dec. 23, 2008, provisional application No. 61/108,096, filed on Oct. 24, 2008, provisional application No. 61/108,097, filed on Oct. 24, 2008.

(51) Int. Cl.

| C07C 315/06 | (2006.01) |
|---|---|
| C08G 65/40 | (2006.01) |
| C08G 8/02 | (2006.01) |
| C08G 75/23 | (2006.01) |

(52) U.S. Cl.
CPC ............... C07C 315/06 (2013.01); C08G 8/02 (2013.01); C08G 65/4012 (2013.01); C08G 65/4093 (2013.01); C08G 75/23 (2013.01); C08G 2261/3444 (2013.01)

(58) Field of Classification Search
CPC ........... C08G 75/23; C08G 2261/3444; C08G 65/4093
USPC .................................... 528/125, 126; 568/34
See application file for complete search history.

(56) References Cited

U.S. PATENT DOCUMENTS

| 3,928,295 A | 12/1975 | Rose |
| 3,953,400 A | 4/1976 | Dahl |
| 3,956,240 A | 5/1976 | Dahl et al. |
| 4,113,698 A | 9/1978 | Staniland |
| 4,176,222 A | 11/1979 | Cinderey et al. |
| 4,837,296 A | 6/1989 | Heinz et al. |
| 5,051,495 A | 9/1991 | Staniland et al. |
| RE34,085 E | 9/1992 | Rose et al. |
| 5,169,923 A | 12/1992 | Hay et al. |
| 5,777,172 A * | 7/1998 | Standen et al. ............... 568/332 |
| 2005/0010015 A1 | 1/2005 | Zhang et al. |
| 2007/0142613 A1 | 6/2007 | Hung et al. |

FOREIGN PATENT DOCUMENTS

| EP | 0211693 A1 | 2/1987 |
| EP | 275035 A2 | 7/1988 |
| EP | 323076 A2 | 7/1989 |
| JP | 2004-315764 A | 11/2004 |
| JP | 2007-238890 A | 9/2007 |
| WO | 0119896 A1 | 3/2001 |
| WO | 02075835 A2 | 9/2002 |
| WO | 2009021918 A1 | 2/2009 |
| WO | 2010046483 A1 | 4/2010 |
| WO | 2010046484 A1 | 4/2010 |
| WO | 2010046487 A1 | 4/2010 |

OTHER PUBLICATIONS

Mullin, John W.—"Crystallization and Precipitation", Ullmann's Encyclopedia of Industrial Chemistry, Online Edition 2005, Wiley-VCH Verlag GmbH & Co. KGaA, Weinheim, pp. 1-51; 51 pgs.

Nassau, Kurt—"Color", Kirk-Othmer Encyclopedia of Chemical Technology, 2004, vol. 7, John Wiley & Sons, Inc., pp. 303-341; 39 pgs.

Davies, Reg—"Sampling", Kirk-Othmer Encyclopedia of Chemical Technology, Online Edition 2000, John Wiley & Sons, Inc., pp. 1-22; 22 pgs.

* cited by examiner

*Primary Examiner* — Shane Fang
(74) *Attorney, Agent, or Firm* — Osha Liang LLP

(57) ABSTRACT

The presence of certain impurities in diphenyl sulfone have a deleterious effect on the properties of the poly(aryletherketone)s produced therein, including one or more of color, melt stability, molecular weight, crystallinity, etc. and here identify those impurities and provide processes for the recovery of the diphenyl sulfone.

11 Claims, No Drawings

HIGH PURITY DIPHENYL SULFONE, PREPARATION AND USE THEREOF FOR THE PREPARATION OF A POLY(ARYLETHERKETONE)

CROSS REFERENCE TO RELATED APPLICATIONS

The present application claims the priority benefit to U.S. provisional application No. 61/108,096 filed on Oct. 24, 2008, to U.S. provisional application No. 61/108,097 filed on Oct. 24, 2008, and to U.S. provisional application No. 61/140,205 filed on Dec. 23, 2008, the whole content of all these applications being herein incorporated by reference for all purposes.

FIELD OF THE INVENTION

This invention relates to highly pure diphenyl sulfone, process for the production of such high purity solvent and its use in a method for the preparation of improved poly(aryl ether ketone) polymers by aromatic nucleophilic substitution.

BACKGROUND OF THE INVENTION

Poly(aryl ether ketone) polymers (i.e., PAEK polymers) are a well known class of engineering polymers useful in various fields of endeavor whose structures combine both ether and ketone groups. Poly(etheretherketone) (PEEK) and poly(etherketone) (PEK) are the most common PAEK. PEK and PEEK are high-strength, radiation-resistant engineering plastics, thermally stable and highly resistant to chemicals.

Processes for preparing these polymers can be found in, e.g., U.S. Pat. Nos. 3,953,400, 3,956,240, 3,928,295, and 4,176,222, all incorporated herein by reference. Generally, PAEK polymers are prepared by aromatic nucleophilic substitution. For example, a bisphenol can be used as a nucleophilic component which is deprotonated with a base such as NaOH, $Na_2CO_3$ or $K_2CO_3$. The resultant bisphenolate may then react with a bishalogenated monomer, e.g., a dihalobenzophenone such as difluorobenzophenone to form PEEK via nucleophilic substitution, with the halogen atoms of the dihalobenzophenone acting as leaving groups. For high temperature processes (i.e. requiring reaction temperatures higher than 250° C., more particularly more than 300° C.), fluorine is the preferred halogen. Examples of fluorinated monomers are represented by structures 1 to 6 (4,4'-difluorobenzophenone (1), 1,4-bis(4'-fluorobenzoyl)benzene (2), 1,3-bis(4'-fluorobenzoyl)benzene (3), etc). Often, such PAEK reactions are carried out in a solvent that is, or that contains, diphenyl sulfone (DPS). For such high temperature processes, a high purity of solvent is required.

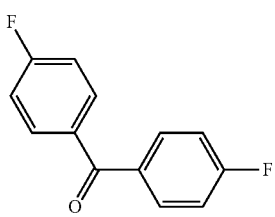

(1)

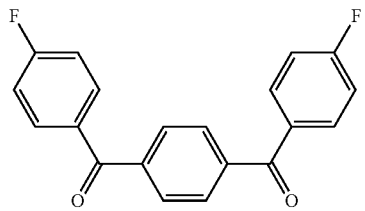

(2)

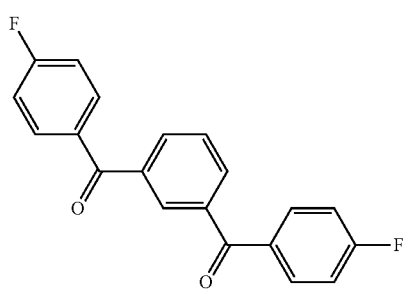

(3)

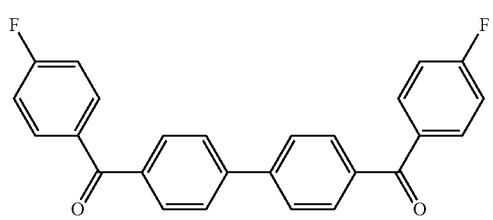

(4)

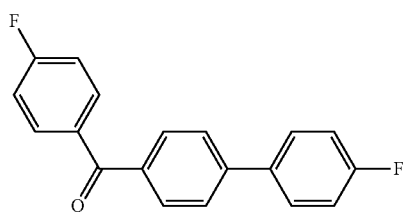

(5)

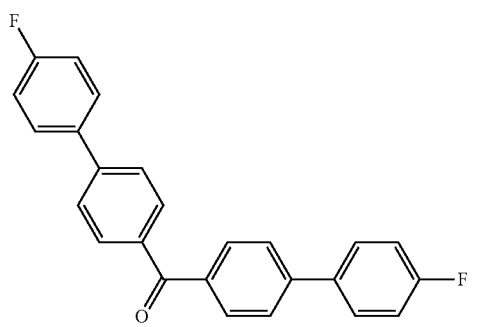

(6)

To the best of the inventor's knowledge, only two documents pertain to the recovery of diphenyl sulfone in a polyether manufacturing process.

In JP 2004/315764, diphenyl sulfone is recovered by precipitation. Besides, a low boiling organic solvent or a mixture of a low boiling organic solvent with water (homo- or heteroazeotrope) on one hand, and water on the other hand are recovered successively by distillation.

In JP 2007/238890, the addition of water is used to help remove low boiling solvent. The presence of high levels of inorganic salts increases the risk of corrosion of the equipment, especially at the high temperatures.

Because the most economically viable processes for manufacturing PAEKs typically involve a recycling of the reaction solvent comprising, consisting essentially of, or consisting of DPS, and given the difficulties of high temperature recovery/ distillation/purification of DPS, a low temperature recovery operation (e.g., <150° C., preferably <70° C., more preferably below 65° C.), which preferably does not involve distillation of the DPS and which provides DPS of high purity is highly desirable.

SUMMARY OF THE INVENTION

Surprisingly, the inventors have found that certain impurities in diphenyl sulfone (DPS) have a deleterious effect on the properties of the PAEKs produced therein, including one or more of color, melt stability, molecular weight, crystallinity, etc. and here identify those impurities and provide processes for the removal of such impurities:

from new or unused DPS (i.e., DPS not previously used in a PAEK reaction or in any other process or application, e.g., commercially available DPS), hereinafter "virgin" DPS, as well as from DPS previously used in PAEK manufacturing or some other process or application, hereinafter "recovered/recycled/reused" DPS or simply "used" DPS.

The present invention is thus related to highly pure DPS.

The present invention is also related to a method for the production of such high purity solvent. In particular, the present invention concerns a method for isolating a solid diphenyl sulfone from a diphenyl sulfone solution obtained in the preparation of a poly(aryletherketone), wherein the diphenyl sulfone solubility in said solution is lowered at a level of at or below 1.5 wt. % by either:

a) addition of a non solvent to the solution; or
b) addition of the solution to a non solvent; or
c) removal of a fraction of low boiling organic solvent present in the solution by a low temperature evaporation process, followed or preceded by addition of a non solvent to the solution; or
d) cooling the solution; or
e) a combination of two or more of a), b), c) and d).

In the above method, the isolated solid diphenyl sulfone is preferably the diphenyl sulfone used in the method for the preparation of a poly(aryletherketone) (PAEK) as detailed hereinafter.

Another aspect of the present invention is related to a method for the preparation of a poly(aryletherketone) in a solvent comprising such highly pure DPS. In particular, the present invention concerns a method for the preparation of a poly(aryletherketone) by aromatic nucleophilic substitution in a solvent comprising a diphenyl sulfone, wherein said diphenyl sulfone meets at least one of the following impurity limitations:

| | |
|---|---|
| Monomethyldiphenylsulfone content (sum of all isomers) | Less than 0.2 area % |
| Monochlorodiphenylsulfone content (sum of all isomers) | Less than 0.08 area % |
| Sodium content | Less than 55 ppm |
| Potassium content | Less than 15 ppm |
| Iron content | Less than 5 ppm |
| Residual acidity content | Less than 2.0 µeq/g |
| Diphenyl sulfide content | Less than 2.0 wt. % |
| APHA of 20 wt. % solution in acetone at 25° C. | Less than 50 |
| Total chlorine content | Less than 120 ppm | where ppm and wt. % are based on the total weight of the diphenyl sulfone and area % represents the ratio of the GC peak area of the impurity of concern over the total area of all GC peaks of the diphenyl sulfone.

The diphenyl sulfone may comprise therein more than 0.03 area % of one or more oligo(aryl ether ketone) impurities, where area % represents the ratio of the LC peak area of the impurity of concern over the total area of all LC peaks of the diphenyl sulfone. The diphenyl sulfone may also comprise at least one fluorinated monomer, such as a fluorinated monomer selected from the group consisting of:

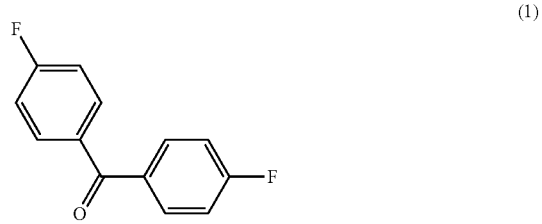

(1)

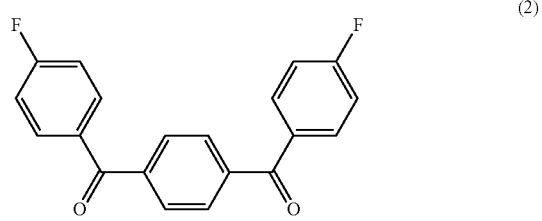

(2)

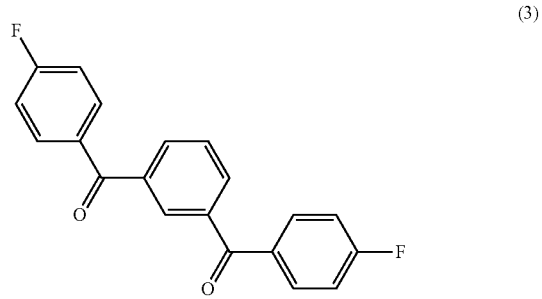

(3)

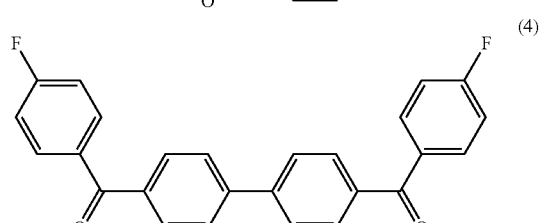

(4)

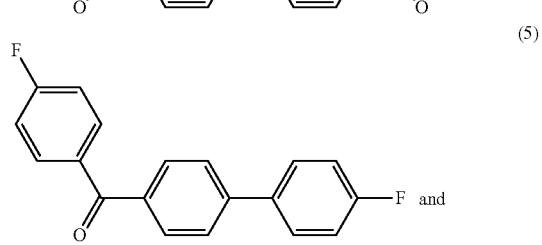

(5)

and

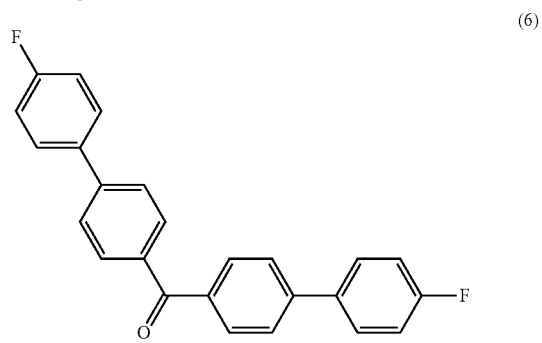

(6)

The diphenyl sulfone meets preferably the impurity limitations for monomethyldiphenylsulfone, monochlorodiphenylsulfone, and residual acidity.

The diphenyl sulfone meets also preferably the impurity limitations for sodium, iron, diphenyl sulfide, and APHA of 20 wt. % solution in acetone at 25° C. Very preferably, it meets further the impurity limitation for potassium.

Preferably, the diphenyl sulfone meets further the following impurity limitation:

| Water content | Less than 0.1 wt. % |
| --- | --- |

The so-prepared poly(aryletherketone) is preferably a poly(ether ether ketone).

The so-prepared poly(aryletherketone), when compression molded at 370° C. into a 2.5 mm thick compression molded plaque, has preferably the following L*, a*, b* values measured under a D65 light source at a 10° angle:
$L^* > 90 - 17^*(\eta_{int})$,
a* is between −1 and +3
b* is between +5 and +20.

Still another aspect of the invention includes a poly(aryletherketone) prepared by a nucleophilic process in highly pure DPS. A related aspect of the invention concerns a poly(aryletherketone) obtainable by the method as above detailed.

Additional aspects and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

DETAILED DESCRIPTION OF THE PREFERRED EMBODIMENTS

The inventors have found that certain impurities in diphenyl sulfone (DPS) have a deleterious effect on the properties of the PAEKs produced therein. Therefore, the diphenyl sulfone according to the present invention contains a low level of such impurities and meets at least one of the following impurity limitations:

| | |
| --- | --- |
| Monomethyldiphenylsulfone content (sum of all isomers) | Less than 0.2 area % |
| Monochlorodiphenylsulfone content (sum of all isomers) | Less than 0.08 area % |
| Sodium content | Less than 55 ppm |
| Potassium content | Less than 15 ppm |
| Iron content | Less than 5 ppm |
| Residual acidity content | Less than 2.0 µeq/g |
| Water content | Less than 0.1 wt. % |
| Diphenyl sulfide content | Less than 2.0 wt. % |
| APHA of 20 wt. % solution in acetone at 25° C. | Less than 50 |
| Total chlorine content | Less than 120 ppm | where ppm and wt. % are based on the total weight of the diphenyl sulfone and area % represents the ratio of the GC peak area of the impurity of concern over the total area of all GC peaks of the diphenyl sulfone.

Such DPS is very useful in the manufacture of PAEK.

The Poly(Aryletherketone)

The term "poly(aryletherketone)" (PAEK) as used herein includes any polymer of which more than 50 wt. % of the recurring units are recurring units (R1) of one or more formulae containing at least one arylene group, at least one ether group (—O—) and at least one ketone group [—C(=O)—].

Preferably, recurring units (R1) are chosen from:

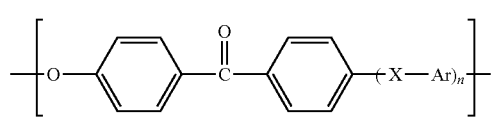

(I)

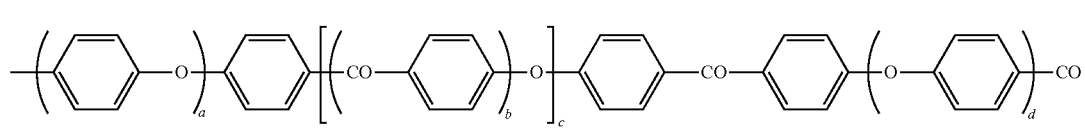

(II)

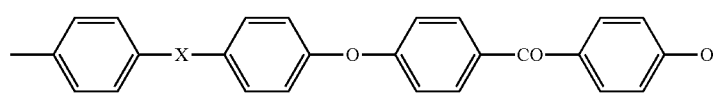

(III)

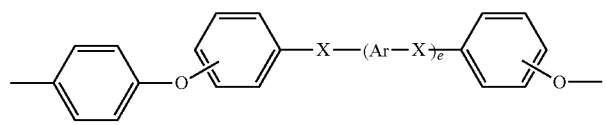

(IV)

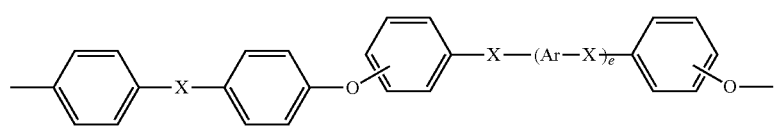

(V)

wherein:
Ar is independently a divalent aromatic radical selected from phenylene, biphenylene or naphthylene,
X is independently O, C(=O) or a direct bond,
n is an integer of from 0 to 3,
b, c, d and e are 0 or 1,
a is an integer of 1 to 4, and
preferably, d is 0 when b is 1.
More preferably, recurring units (R1) are chosen from:
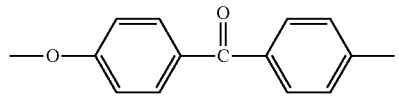
(VI)
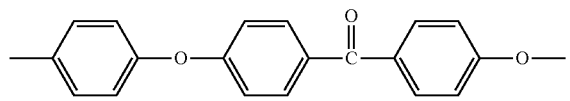
(VII)
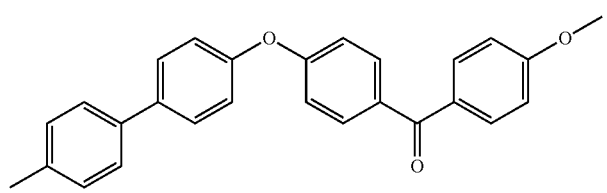
(VIII)
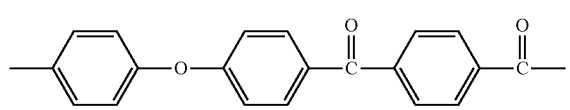
(IX)
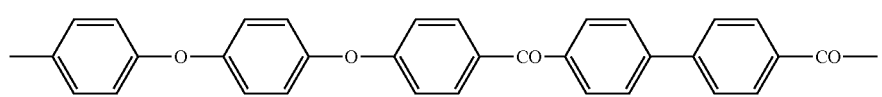
(X)
(XI)
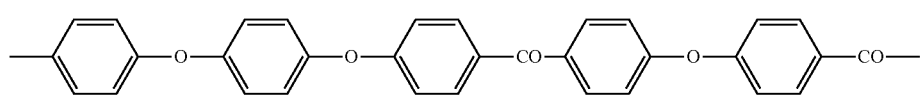
(XII)
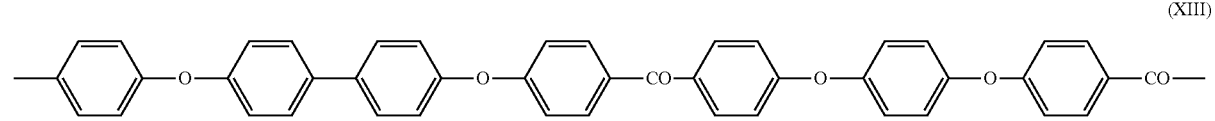
(XIII)
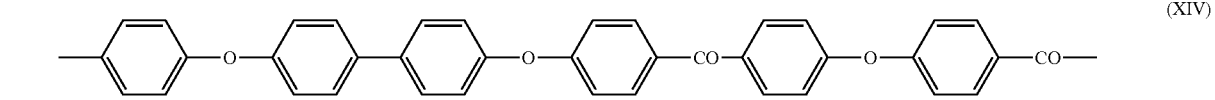
(XIV)
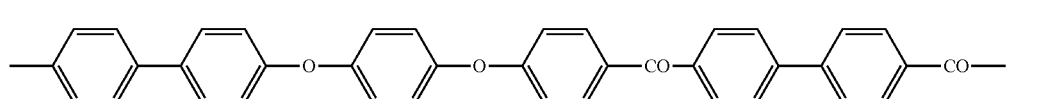
(XV)
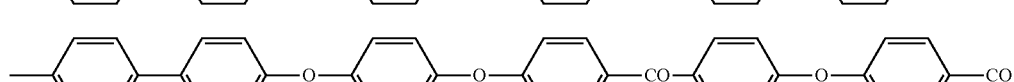
(XVI)
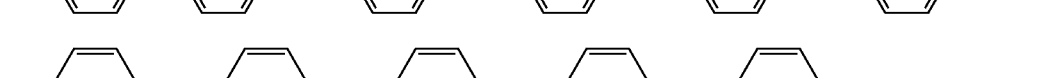
(XVII)
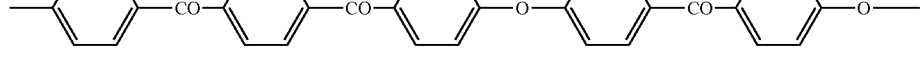
(XVIII)
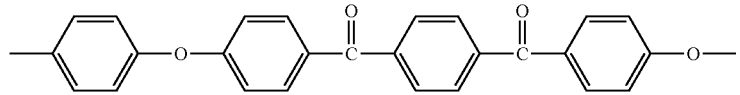

-continued

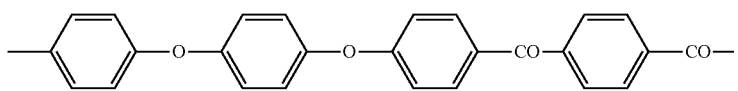
(XIX)

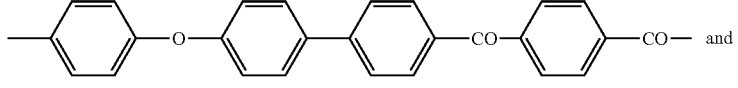
(XX)

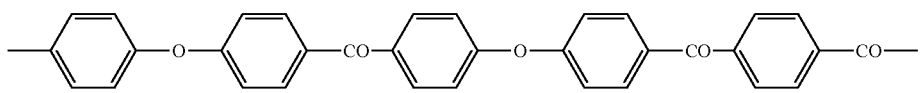
(XXI)

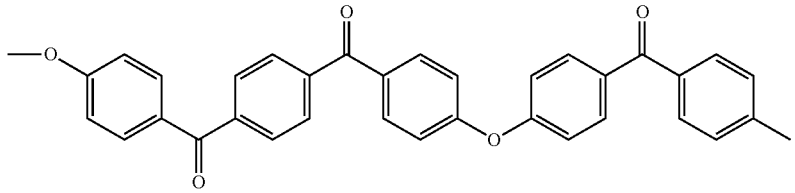
(XXII)

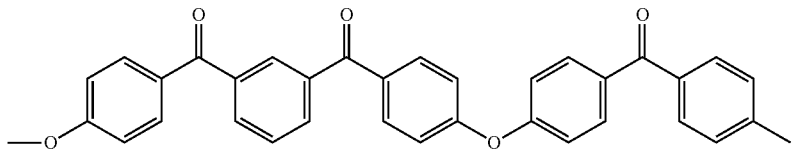
(XXIII)

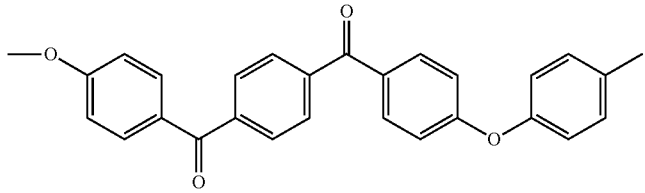
(XXIV)

(XXV)

Still more preferably, recurring (R1) are chosen from:

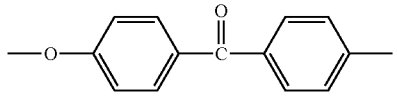
(VI)

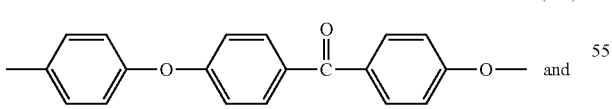
(VII)

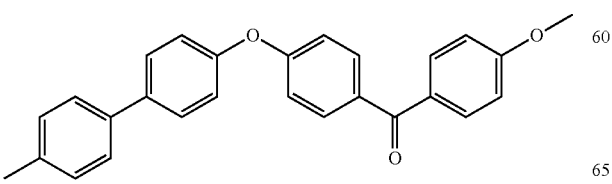
(VIII)

The most preferably, recurring units (R1) are:

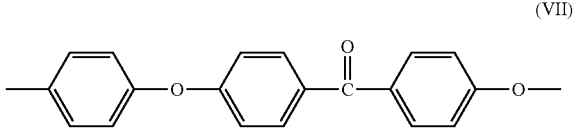
(VII)

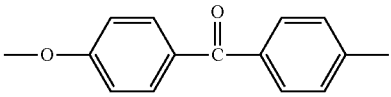
(VI)

A PEEK polymer is intended to denote any polymer of which more than 50 wt. % of the recurring units are recurring units (R1) of formula (VII). A PEK polymer is intended to denote any polymer of which more than 50 wt. % of the recurring units are recurring units (R1) of formula (VI).

The poly(aryletherketone) may be notably a homopolymer, a random, alternate or block copolymer. When the poly (aryletherketone) is a copolymer, it may notably contain (i) recurring units (R1) of at least two different formulae chosen from formulae (VI) to (XXI), or (ii) recurring units (R1) of one or more formulae (VI) to (XXI) and recurring units (R1*) different from recurring units (R1).

Preferably more than 70 wt. %, more preferably more than 85 wt. % of the recurring units of the poly(aryletherketone) are recurring units (R1). Still more preferably, essentially all the recurring units of the poly(aryletherketone) are recurring units (R1). The most preferably, all the recurring units of the poly(aryletherketone) are recurring units (R1).

U.S. Pat. Nos. 3,953,400, 3,956,240, 3,928,295, and 4,176,222, and RE 34,085, all incorporated herein by reference, also disclose PAEKs and methods for their preparation. As noted above, PAEK polymers are generally prepared by aromatic nucleophilic substitution. For example, a bisphenol can be deprotonated with a base such as NaOH, $Na_2CO_3$ or $K_2CO_3$ and the resultant bisphenolate may then react with a bishalogenated monomer, e.g., a dihalobenzophenone via nucleophilic substitution, to form a PAEK via nucleophilic substitution. Such PAEK reactions are typically carried out in a solvent that is, or that contains, diphenyl sulfone.

A dihalobenzophenone of particular interest, since it can be used to form PEEK via nucleophilic substitution (when it is reacted with the phenolate obtained by deprotonating p-hydroquinone), and also many other useful PAEKs [when it is reacted with other bisphenolates such those obtained by deprotonating 4,4'-biphenol, 1,4-bis-(p-hydroxybenzoyl)benzene or 1,3-bis-(p-hydroxybenzoyl)benzene)], is 4,4'-difluorobenzophenone. The Applicant has surprisingly found that, when 4,4'-difluorobenzophenone is used for preparing semi-crystalline poly(aryletherketone) in the process according to the present invention, improved results are obtained when 4,4'-difluorobenzophenone complies with certain impurity limitations.

Embodiment (D)

Hence, in a particular embodiment (D) of the present invention, the invented method for the preparation of a poly(aryletherketone) is a method for the preparation of a semi-crystalline poly(aryl ether ketone) by aromatic nucleophilic substitution in a solvent comprising a diphenyl sulfone, wherein:

said diphenyl sulfone meets at least one of the impurity limitations as described in the present document, and a nucleophile is reacted with a 4,4'-difluorobenzophenone, wherein the 4,4'-difluorobenzophenone meets the following impurity limitation: [2,4'-difluorobenzophenone]+[4-monofluorobenzophenone]≤1250 ppm wherein the amounts of 2,4'-difluorobenzophenone and 4-monofluorobenzophenone in 4,4'-difluorobenzophenone are determined by liquid chromatography analysis.

For example, the liquid chromatography determination can be carried out with a Agilent 1100 LC High Pressure Liquid Chromatography instrument using a Supelco Discovery HS F5, 5 μm, 25 cm×4.6 mm column. Suitable analysis conditions include:

Mobile Phase: acetonitrile/deionized water

Gradient: 60/40 acetonitrile/water for 5 minutes, increase to 100% acetonitrile in a further 10 minutes.

Flow rate: 1 ml/minute

Detection: UV 254 nm

Temperature: 50° C.

Injection Volume: 5 μl

The sample is prepared by dissolving about 0.01 g of 4,4'-difluorobenzophenone in 100 ml of acetone.

The amount of 2,4'-difluorobenzophenone and 4-monofluorobenzophenone in 4,4'-difluorobenzophenone is typically determined using a calibration with three external standards of these commercially available compounds, of different concentrations, to generate a calibration curve. Under the above detailed conditions, the retention time of 2,4'-DFBP is typically about 7.4 minutes and typically about 7.1 minutes for 4-monofluorobenzophenone, while the retention time for 4,4'-DFBP is typically about 7.7 minutes.

Results are expressed as parts per million of the two impurities.

In present embodiment (D), preferably, the 4,4'-difluorobenzophenone further meets the following impurity limitation:

[2,4'-difluorobenzophenone]≤750 ppm, and, more preferably, it further meets at least one of the following sets of impurity limitations:

Set 1: [2,4'-difluorobenzophenone]≤750 ppm, and [4-monofluorobenzophenone]≤500 ppm, Set 2: [2,4'-difluorobenzophenone]≤300 ppm, and [4-monofluorobenzophenone]≤950 ppm.

PAEK polymers that were prepared in accordance with embodiment (D) exhibited improved properties, including improved chemical resistance, improved mechanical properties over a large temperature range, improved crystallinity and/or melt stability.

The Diphenyl Sulfone

DPS that meets one or more of the specific impurity limits described herein, including DPS that meets one or more of the impurity limits described herein by having undergone a purification according to the invention, is called purified DPS or highly pure DPS.

In their preparation of highly pure DPS the inventors have determined that commercially available diphenyl sulfone contains several impurities, including monomethyldiphenylsulfone (several isomers), monochlorodiphenylsulfone (several isomers), sodium chloride, potassium chloride, sodium sulfate, potassium sulfate, iron salts, water, sulfuric acid and benzene sulfonic acid.

In addition, when DPS is used in a manufacturing process for PAEK and is then recycled or reused, impurities that are generally present in DPS include:

low boiling extraction solvent(s) used during the polymer isolation process (e.g., acetone, methanol, ethanol, monochlorobenzene, xylene, etc);

salts resulting from the manufacturing process (this includes the polymer isolation steps): typically these can be sodium fluoride, potassium fluoride, sodium chloride, potassium chloride, lithium fluoride, sodium carbonate and potassium carbonate;

water;

organic or inorganic impurities arising form thermal degradation of diphenyl sulfone, including diphenyl sulfide, biphenyl, dibenzothiophene sulfone, benzene sulfinic acid, benzene sulfonic acid, biphenyl phenyl sulfone (several isomers), $SO_2$;

residual oligo(aryl ether ketone)s, mostly with fluorine, chlorine, hydroxyl end groups or with no end groups (cyclic);

residual monomers, present either in their neutral form or in their ionized form (e.g. bisphenolate salt);

residual chemicals originating from the polymer purification process (e.g. inorganic acid like HCl).

Certain of these impurities have been identified as having a negative impact on the properties of the PAEKs obtained from regular (i.e. non purified) virgin or used DPS.

Usually, the recovered DPS does contain some residual fluorinated monomer.

Fluorinated monomer (1) to (6) are one of these impurities. The presence of fluorinated monomers (1) and (2) is preferred. Fluorinated monomer concentration is usually higher than 50 ppm and can be as high 5 wt. %. It is economically advantageous to maximize recycling of monomer.

Usually, the recovered DPS also contains impurities formed during the PAEK synthesis reaction. More particularly, the recovered DPS can contain residual oligo(aryl ether ketone)s. Oligo(aryl ether ketone)s found in recovered DPS result from the reaction of m molecules of fluorinated monomer with n molecules of bisphenols wherein m=n or n+1 and m≤5. Oligo(aryl ether ketone)s, which can be found in the recovered DPS, have thus generally a structure similar to PAEK produced, but with a lower degree of polymerization. Typically, the degree of polymerization is such that these oligo(aryl ether ketone)s are soluble in the low boiling solvent used for extraction. Preferably, these oligo(aryl ether ketone)s have a degree of polymerization of maximum 5, more preferably maximum 4, the most preferably maximum 3. Degrees of polymerizations of 1.5, 2.5 are also possible. Oligo(aryl ether ketone)s with a degree of polymerization higher than five can also be present in the recovered diphenyl sulfone. The degree of polymerization is the number of recurring units (R1) in the molecule. Non integer numbers are used when one bifunctional monomer has reacted in excess of the other bifunctional monomer. Mostly the oligo(aryl ether ketone)s have exactly the same recurring unit (R1) as the PAEK they are derived from but, in some instances, the oligo (aryl ether ketone)s can have a recurring unit different, formed by side-reactions during the polymerization reaction or during the DPS recovery process.

Usually, residual oligo(aryl ether ketone)s found in recovered DPS have either fluorine or chlorine end groups, hydroxyl or ionized end groups or no reactive end groups at all. The later oligo(aryl ether ketone)s with no reactive end groups include cyclic oligo(aryl ether ketone)s, oligo(aryl ether ketone)s featuring hydrogen end groups (—H) and oligo(aryl ether ketone)s featuring phenyl ether end groups (—O-Ph).

The presence of certain specific oligo(aryl ether ketone)s have been identified as detrimental to the synthesis of PAEK. For example, oligo(aryl ether ketone)s with hydroxyl or ionized end groups tend to alter the color of recovered diphenyl sulfone, as measured by the color of a 20% solution in acetone.

On the other hand, the Applicant has surprisingly found that the presence of oligo(aryl ether ketone)s with fluorine or chlorine end groups or cyclic oligo(aryl ether ketone)s has only very limited or even no negative effect at all. In particular, the Applicant has surprisingly found that the presence of cyclic oligo(aryl ether ketone)s has essentially no negative effect or no negative effect at all.

Then, if present, the oligo(aryl ether ketone)s are preferably present according to the following relationship: cyclic oligo(aryl ether ketone)s are preferred to oligo(aryl ether ketone)s featuring hydrogen end groups (—H) and oligo(aryl ether ketone)s featuring phenyl ether end groups (—O-Ph), which are preferred to oligo(aryl ether ketone)s featuring fluorine end groups, which are preferred to oligo(aryl ether ketone)s featuring chlorine end groups, which are preferred to oligo(aryl ether ketone)s featuring hydroxyl or ionized end groups. In other words, the DPS according to the present invention is preferably essentially free or free of oligo(aryl ether ketone)s with hydroxyl or ionized end groups.

Examples of oligo(aryl ether ketone)s that are often present in recovered DPS used to prepare PAEK of recurring unit (R1) of formula (VII) are shown in structures (7) to (11). Oligo(aryl ether ketone)s (10) and (11) are typically formed by a side reaction and contain some recurring units (R1) of formula (VI).

(7)

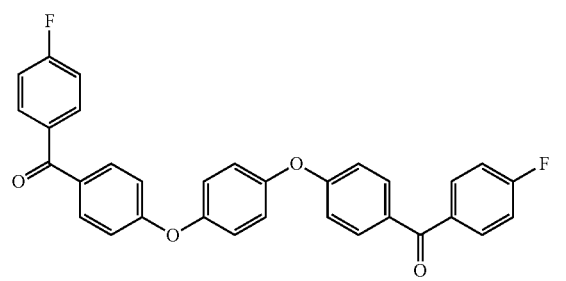

(8)

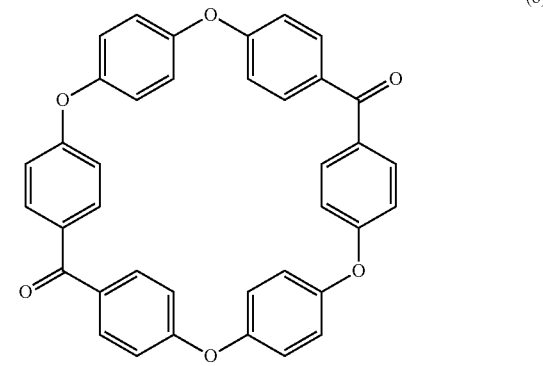

(9)

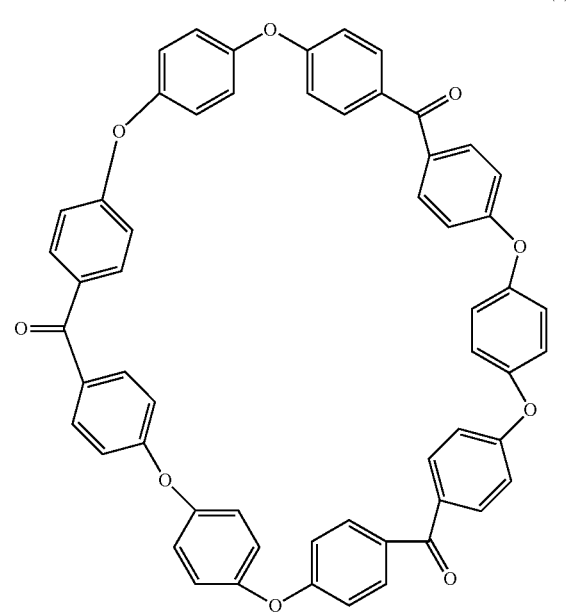

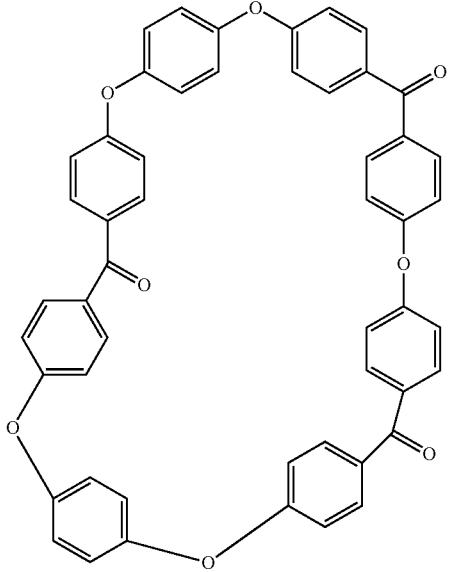

(10)

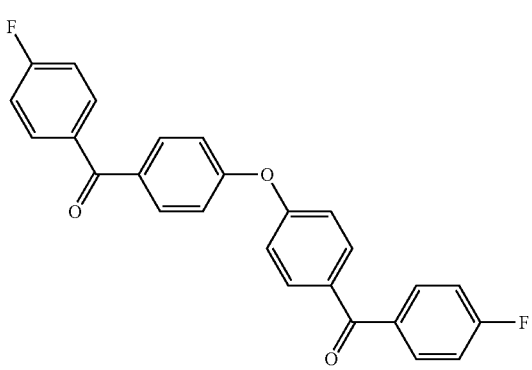

(11)

The DPS according to the present invention, meeting at least one impurity limit (maximum allowable content/Purity Standard) set forth above, can thus comprise therein at least one oligo(aryl ether ketone), such as those described in formulae (7) to (11). The oligo(aryl ether ketone)s can be detected by LC as described in the examples. The amount of such oligo(aryl ether ketone)s is not limited, and can range for example from 0.03 area % to 3 area %, as measured in the examples. In particular, in recovered DPS used to prepare PAEK having recurring units (R1) of formula (VII), the amount of such oligo(aryl ether ketone)s of formulae (7) to (11) can range from 0.03 area % to 3 area %, as measured in the examples. Area % represents the ratio of the LC peak area of the impurity of concern over the total area of all LC peaks of the DPS.

The DPS according to the present invention can comprise either more than 0.03 area % of one or more oligo(aryl ether ketone)s, or higher than 0.1 area %, or higher than 0.5 area %, or even higher than 1.0 area %, based on the total LC peak area of the diphenyl sulfone plus impurities. On the other hand, and to the extent that certain oligo(aryl ether ketone)s, such as oligo(aryl ether ketone)s with hydroxyl or ionized end groups, are detrimental to the synthesis of PAEK, it is beneficial to limit the amount of oligo(aryl ether ketone)s in general to an amount lower than 5 area %, more preferably lower than 4 area %, still more preferably lower than 3 area % and the most preferably lower than 2 area %.

On the other hand, since other oligo(aryl ether ketone)s have only very limited effect, essentially no effect or even no negative effect at all, such as the oligo(aryl ether ketone)s of formulae (7) to (11), the skilled person will advantageously spend no effort to remove specifically these oligo(aryl ether ketone)s. Thus, the DPS according to the present invention comprises preferably more than 0.03 area %, more preferably higher than 0.1 area %, still more preferably higher than 0.5 area %, and the most preferably higher than 1.0 area %, based on the total LC peak area of the diphenyl sulfone plus impurities, of one or more oligo(aryl ether ketone)s selected from the group consisting of cyclic oligo(aryl ether ketone)s, oligo (aryl ether ketone)s featuring hydrogen end groups (—H), oligo(aryl ether ketone)s featuring phenyl ether end groups (—O-Ph), and oligo(aryl ether ketone)s featuring fluorine end groups. In particular, the DPS according to the present invention comprises preferably more than 0.03 area %, more preferably higher than 0.1 area %, still more preferably higher than 0.5 area %, and the most preferably higher than 1.0 area %, based on the total LC peak area of the diphenyl sulfone plus impurities, of one or oligo(aryl ether ketone)s selected from the group consisting of oligo(aryl ether ketone)s of formulae (7) to (11), more particularly the group consisting of oligo(aryl ether ketone)s of formulae (7), (8) and (11). Besides, the DPS according to the present invention comprises preferably more than 0.01 area %, more preferably higher than 0.03 area %, still more preferably higher than 0.1 area %, and the most preferably higher than 0.3 area %, based on the total LC peak area of the diphenyl sulfone plus impurities, of one or more cyclic oligo(aryl ether ketone)s, in particular the cyclic oligo(aryl ether ketone)s of formulae (8) to (10), more particularly the cyclic oligo(aryl ether ketone) of formula (10). The amount of any oligo(aryl ether ketone) or of any group of oligo(aryl ether ketone) cited in the present paragraph may be either lower than 5 area %, or lower than 4 area %, or lower than 3 area %, or lower than 2 area %.

The DPS according to the present invention, meeting at least one impurity limit (maximum allowable content/Purity Standard) set forth above, may comprise at least one low boiling extraction solvent. It contains preferably less than 1 wt. %, more preferably less than 0.5 wt. %, the most preferably less than 0.2 wt. % of such low boiling extraction solvent.

The DPS according to the present invention, meeting at least one impurity limit (maximum allowable content/Purity Standard) set forth above, may comprise at least one organic or inorganic impurities arising from thermal degradation of diphenyl sulfone. It contains preferably less than 3 area %, more preferably less than 2 area % of such impurities.

The present invention relates, in part, to the purification of DPS and the use thereof of the purified product. Diphenyl sulfone (DPS) is a high boiling solvent (b.p.=389° C. under atmosphere pressure) with a high melting point (125-129° C.). Currently, the presence of certain impurities in DPS requires the use of special construction materials for the recovery operation or for storage in the molten stage to limit corrosion. Moreover, the present inventors have found that certain impurities in DPS have a deleterious effect on the properties of the PAEKs produced therein, including color, melt stability, molecular weight, crystallinity, etc., the extent of the impact of these impurities depending on the concentration at which the polymerization reaction is run. Preferably, the polymerization reaction is done with a ratio of DPS solvent to polymer made at least of 1.45 kg DPS/kg polymer made, more preferably at least of 1.50 kg/kg polymer made. Preferably, the amount of DPS solvent used is no more than 2.60 kg DPS/kg polymer. More preferably, the amount of DPS used is no more than 2.50 kg/kg polymer made.

After much study, it has been determined that both virgin and recovered/recycled/reused DPS, when purified to meet at least one, preferably two or more, and the most preferably all, of the following impurity limits (maximum allowable content/Purity Standard), avoid the problems identified above with regard to PAEK properties (the following Table of purity standards shows a maximum allowable level of the identified impurity, and a non-exhaustive list of PAEK properties affected):

| Limitation | Impurity or analysis | Maximum allowable content (Purity Standard) | Polymer property affected/Process aspect |
|---|---|---|---|
| α | Monomethyldiphenylsulfone (sum of all isomers) | 0.2 area % | Molecular weight |
| β | Monochlorodiphenylsulfone (sum of all isomers) | 0.08 area % | Molecular weight, color |
| γ | Sodium | 55 ppm | Molecular weight, color, melt stability |
| δ | Potassium | 15 ppm | Molecular weight, color, melt stability |
| ε | Iron | 5 ppm | Color, crystallinity |
| ζ | Residual acidity | 2.0 μeq/g | Molecular weight, color, corrosion |
| η | Water | 0.1 wt. % | Molecular weight, color, corrosion |
| θ | Diphenyl sulfide | 2.0 wt. % | Color |
| ι | APHA of 20 wt. % solution in acetone at 25° C. | 50 | Color |
| κ | Total chlorine | 120 ppm | Molecular weight, color corrosion |

These identified maximum allowable limits include the full range of values from zero to (and including) the maximum allowable content, and all values and subranges within this range as if written out. In the above Table and wherever present herein, ppm and wt. % are based on the total weight of the diphenyl sulfone (i.e. the 100% pure DPS+all present impurities) and area % represents the ratio of the GC peak area of the impurity of concern over the total area of all GC peaks of the diphenyl sulfone. Generally chromatographic data is presented as a graph of detector response (y-axis) against retention time (x-axis). This provides a spectrum of peaks for a sample representing the analytes present in a sample eluting from the column at different times. Retention time can be used to identify analytes if the method conditions are constant. Also, the pattern of peaks will be constant for a sample under constant conditions and can identify complex mixtures of analytes. In most modern applications however the GC is connected to a mass spectrometer or similar detector that is capable of identifying the analytes represented by the peaks. The area under a peak is proportional to the amount of analyte present. By calculating the area of the peak using the mathematical function of integration, the concentration of an analyte in the original sample can be determined. In most modern systems, computer software is used to draw and integrate peaks. For organic impurities, for which more than one isomer is possible (monomethyldiphenylsulfone and monochlorodiphenylsulfone), the impurity requirement pertains to the total concentration of all the impurity isomers.

Monomethyldiphenylsulfone (sum of all isomers) is advantageously present in an amount of less than 0.2 area % (limitation α), preferably less than 0.18 area %, more preferably less than 0.14 area %, still more preferably less than 0.1 area % and the most preferably less than 0.08 area %.

Monochlorodiphenylsulfone (sum of all isomers) is advantageously present in an amount of less than 0.08 area % (limitation β), preferably less than 0.07 area %, more preferably less than 0.06 area %, still more preferably less than 0.05 area % and the most preferably less than 0.04 area %.

Sodium is advantageously present in an amount of less than 55 ppm (limitation γ), preferably less than 50, more preferably less than 40, still more preferably less than 30 and the most preferably less than 25 ppm.

Potassium is advantageously present in an amount of less than 15 ppm (limitation δ), preferably less than 14, more preferably less than 12, still more preferably less than 10 and the most preferably less than 8 ppm.

Iron is advantageously present in an amount of less than 5 ppm (limitation ε), preferably less than 4, more preferably less than 3, still more preferably less than 2 and the most preferably less than 1 ppm.

Residual acidity is advantageously present in an amount of less than 2.0 μeq/g (limitation ζ), preferably less than 1.8, more preferably less than 1.6, still more preferably less than 1.4 and the most preferably less than 1 μeq/g.

Water is advantageously present in an amount of less than 0.1 wt. % (limitation η), preferably less than 0.09, more preferably less than 0.08, still more preferably less than 0.07 and the most preferably less than 0.06 wt. %.

Diphenyl sulfide is advantageously present in an amount of less than 2 wt. % (limitation θ), preferably less than 1.6, more preferably less than 1.2, still more preferably less than 0.8 and the most preferably less than 0.4 wt. %.

The APHA value of 20 wt. % solution in acetone at 25° C. is s advantageously of less than 50 (limitation ι), preferably less than 45, more preferably less than 40, still more preferably less than 35 and the most preferably less than 30.

Total chlorine content is advantageously of less than 120 ppm (limitation κ), preferably less than 115, more preferably less than 110, still more preferably less than 105 and the most preferably less than 100 ppm.

In a preferred embodiment, the DPS is pure in a way such that it meets one or more of the following groups of several impurity limits (maximum allowable content/Purity Standard) noted above:
1.) Monomethyldiphenylsulfone (sum of all isomers), monochlorodiphenylsulfone (sum of all isomers), residual acidity, water
2.) sodium, iron, diphenyl sulfide, APHA of 20 wt. % solution in acetone at 25° C.
3.) sodium, potassium, iron, diphenyl sulfide, APHA of 20 wt. % solution in acetone at 25° C.

In other words, the DPS according to the present invention meets preferably the above described α and β limitations, more preferably the above described α, β and ζ limitations, still more preferably the above described α, β, ζ and η limitations. It meets also preferably the above described γ and ε limitations, more preferably the above described γ, ε and θ limitations, still more preferably the above described γ, ε, θ and ι limitations and the most preferably the above described γ, ε, θ, ι and δ limitations.

Also in a preferred embodiment, the DPS according to the invention has a minimal amount of diphenyl sulfide present (λ limitation), yet meets the above impurity limit. The diphenyl sulfone according to the present invention contains preferably more than 0.0025, more preferably more than 0.005, still more preferably more than 0.01, 0.05, 0.1, and the most preferably more than 0.2 wt. % diphenyl sulfide. On the other hand, it contains advantageously less than 2.0 wt. %, preferably less than 1.8, more preferably less than 1.6 still more preferably less than 1.4 and the most preferably less than 1.2 wt. % diphenyl sulfide.

The DPS according to the present invention meets at least one of the above described α to λ impurity limitations, it meets preferably at least two, more preferably at least three, still more preferably at least four and the most preferably at least five of the above described α to λ impurity limitations. Excellent results were obtained when the DPS according to the present invention met almost all or even all the above described α to λ impurity limitations.

The highly pure DPS according to the present invention may in fact be seen as a composition of matter comprising pure DPS and optionally one or more impurities. Accordingly, the GC chromatogram of the highly pure DPS according to the present invention comprise one major peak related to pure DPS and optionally one or more smaller peaks related to the optional one or more impurities.

Any method of solvent purification can be used in purifying virgin and used DPS so as to meet the above purity standard(s). Such techniques include distillation, liquid and gas chromatography, adsorption and/or absorption on silica or other solid media, ion exchange techniques, extraction, (re)crystallization, precipitation, etc. Combinations of such methods may be used. Those of ordinary skill in the art know how to measure, and are capable of measuring, the amount of the impurities noted above that are present in the purified DPS to determine whether the invention maximum allowable content of a given impurity has been met. Purifying used and virgin DPS using such techniques is a routine matter in the art, as is the measurement of the noted impurities. Thus, given the disclosure herein, one of ordinary skill can purify DPS according to the invention, can provide purified DPS, and can provide purified DPS meeting one or more of the above purity standards.

With regard to recovered/recycled/reused DPS that has been used in the preparation of a PAEK, the recovery of DPS according to the invention typically involves isolating DPS from a DPS mixture comprising at least one of the following: at least one low boiling organic solvent, water, one or more inorganic salts like chlorides, fluorides and carbonates, residual monomer(s), and residual oligo(aryl ether ketone)s. This DPS mixture is hereinafter termed a "DPS solution" or simply "extract". Typically, the water content in these extracts is between 0.5 and 15 wt. %.

In a typical example, a DPS extract is obtained in the preparation of a PAEK as follows. The reaction mixture, comprising DPS, PAEK, salts, fluorinated monomers, oligo (aryl ether ketone)s, etc, is solidified at the end of the polymerization reaction by cooling and ground to the target particle size. A preferred range of mean particle size (D50) is between 100 and 2500 μm, and more preferably between 200 and 2000 μm. The reaction solvent, DPS, is then separated from the polymer by extraction with a low boiling organic solvent (acetone, methanol, ethanol, chlorobenzene, xylene or their mixtures). The low boiling organic solvent can be either virgin or recycled. Salts present in the reaction mixture are also partially extracted with the organic solvent, as well as DPS, fluorinated monomers and oligo(aryl ether ketone)s. These extracts also contain water, present in the low boiling solvent used for extraction and/or present in the reaction mixture as a result of a previous washing step with water. The extraction process can be carried out at room temperature or a temperature higher than room temperature, for instance at the boiling point of the low boiling organic solvent. The so-separated PAEK and salts may then be further washed with another solvent, water or mixtures thereof to extract remaining water, low boiling organic solvent, salts, chemicals . . . to finally lead to the obtention of the PAEK.

The invention low temperature processes for purifying DPS solution generally involve isolating solid diphenyl sulfone from the solution in which the diphenyl sulfone solubility is preferably at or below 1.5 wt. % at the temperature at which the purification is done, more preferably at or below 1.2 wt. %, still more preferably at or below 1 wt. %. In order to keep the organic impurities in solution, the solubility of the DPS is preferably at or higher than 0.02 wt. %, more preferably higher than 0.05, still more preferably higher than 0.08 and the most preferably higher than 0.12. Thus, DPS solubility in this solution is preferably 0.05-1.5 wt. %, including all values and subranges therebetween, such as 0.06, 0.1, 0.5, 0.55, 0.7, 0.9, 1.2, 0.6-1.3, etc. wt. %.

Different approaches can be used according to the invention, each one of them taken alone or in combination:
1. Addition of a non solvent to the solution, or more preferably, addition of the solution to a non solvent. A non solvent is a solvent in which DPS solubility is lower than 10 wt. %, typically less than 5 wt. % at the temperature at which the purification is operated. Non solvents include water, methanol, ethanol, etc and mixtures thereof. The ratio of the non solvent/solution is selected such that the final solubility of DPS is preferably below 1.5 wt. % at the purification temperature. This operation is preferably carried out under vigorous agitation. Examples of precipitation procedures and equipment, well known to the persons skilled in the art, can be found in "Crystallization and Precipitation", J. Mullin, "Ullmann's Encyclopedia of Industrial Chemistry", Online Ed. 2005.
2. Removal of a fraction of the low boiling organic solvent contained in the solution by a low temperature evaporation process (below 150° C., the actual temperature depends on the low boiling solvent boiling point. The evaporation step is advantageously done under subatmospheric pressure.), followed or preceded by a step of addition of a non solvent to reach the solubility limits outlined above (i.e., 0.05-1.5 wt. %). This can be done for example in an agitated vessel or other means known to the person skilled in the art. Examples of evaporation technology can be found in "Evaporation", R. Billet in "Ullmann's Encyclopedia of Industrial Chemistry", online Ed, 2005. In order to limit thermal degradation of organic impurities and corrosion of the equipment, a film evaporator is preferred for the low temperature evaporation process. An agitated thin film evaporator is specially preferred. Thin film evaporators present the advantages of low residence time and low wall temperature on the product side. Residence time depends on the separation to conduct. Residence time in thin film evaporators can be as low as fractions of seconds. Preferred residence time is shorter than 15 hours, preferably shorter than 10 hours. This can be carried out in a wiped-film evaporator, for example. Alternatively, the low temperature evaporation process can be accomplished under vacuum. More preferably, the low temperature evaporation process can be carried out in wiped-film evaporator operating under vacuum.
3. Cooling the solution to a temperature at which the solubility of DPS in the solution is less than 1.5 wt. %, preferably in the range of 0.05 wt. %-1.5 wt. %. This is preferred when the solution is initially at a temperature higher than room temperature, for instance with low boiling organic solvents like chlorobenzene, p-xylene, etc.

Of course, any combination of methods 1 to 3 may be used as well. The invention low temperature recovery operations described above are preferably carried out at temperatures of 150° C. or less, more preferably 120° C. or less, still more preferably 100° C. or less and the most preferably 70° C. or less, including 140, 130, 111, 100, 90, 65, 55, 45, 32, 25, 20, 10, 0, etc. ° C. and all values and subranges therebetween. The invention low temperature recovery operations described above are preferably carried out at temperatures above −10° C., preferably above 0° C. The low temperature methods 1-3 preferably do not involve distillation of the DPS.

Another aspect of the present invention is thus related to a method for isolating a solid diphenyl sulfone from a diphenyl sulfone solution obtained in the preparation of a PAEK, wherein the diphenyl sulfone solubility in said solvent is lowered at a level of at or below 1.5 wt. % by either:
a) addition of a non solvent to the solution; or
b) addition of the solution to a non solvent; or
c) removal of a fraction of low boiling organic solvent present in the solution by a low temperature evaporation process, followed or preceded by addition of a non solvent to the solution; or
d) cooling the solution; or
e) a combination of two or more of a), b), c) and d).

The solid DPS provided by the above methods can be separated from the solution by any method, including filtration, centrifuging, etc. The separation preferably is accomplished at 150° C. or less, more preferably 120° C. or less, still more preferably 100° C. or less and the most preferably 70° C. or less, including 140, 130, 111, 100, 90, 65, 55, 45, 32, 25, 20, 10, 0, etc. ° C. and all values and subranges therebetween. The separation is preferably carried out at temperatures above −10° C., preferably above 0° C. The solid DPS obtained may contain unreacted bishalogenated monomer (see examples of structures on page 2), for instance 4,4'-difluorobenzophenone or 1,4-bis(4'-fluorobenzoyl)benzene, 1,3-bis(4'-fluorobenzoyl)benzene monomer depending on the content in the DPS solution and the method chosen. It is economically advantageous to be able to recycle a fraction of unreacted fluorinated monomer.

The solid DPS obtained may contain the above described oligo(aryl ether ketone)s.

After this separation the isolated DPS solid can be further purified if desired. Since the most corrosive impurities have been removed at this stage, this secondary purification can be performed at high temperature or a at low temperature, for example by washing with a non solvent, dissolution in a solvent a high temperature and recrystallization at low temperature, distillation preferably under vacuum, etc.

According to the invention, when a PAEK polymer is made in purified DPS the polymer prepared typically has a molecular weight useful industrially, e.g., intrinsic viscosity $\eta_{int}$>0.62 dl/g in methanesulfonic acid at 30° C., and a low color. The color is generally characterized by L*, a*, b* values, which are tristimulus coordinates defined by the CIE (Commission Internationale de l'Eclairage) in 1976 (K. Nassau, in "Kirk-Othmer Encyclopedia of Chemical Technology", 2004, Chapter 7, P 303-341). These three basic coordinates represent the lightness of the color (L*, L*=0 yields black and L*=100 indicates white), its position between red/magenta and green (a*, negative values indicate green while positive values indicate magenta) and its position between yellow and blue (b*, negative values indicate blue and positive values indicate yellow). L* is measured according to ASTM E308 using D 65 illuminant.

The PAEK polymer made in purified DPS according to the invention has a color, as defined in U.S. Ser. No. 60/955,042, incorporated herein by reference, i.e., a compression molded plaque (2.5 mm thick obtained by compression molding at 370° C.) has the following L*, a*, b* values measured under D65 light source at 10° angle:
L*>90−17*($\eta_{int}$), preferably L*>95−17*($\eta_{int}$)
a* is between −1 and +3
b* is between +5 and +20.

In a preferred embodiment herein, the DPS of the invention, meeting at least one impurity limit (maximum allowable content/Purity Standard) set forth above, comprises therein at least one fluorinated monomer, preferably a fluorinated monomer useful in the preparation of PAEKs, such as 4,4'-difluorobenzophenone monomer, 1,4-bis(4'-fluorobenzoyl)benzene, 1,3-bis(4'-fluorobenzoyl)benzene, etc. Said fluorinated monomer is preferably selected from the group consisting of the above described formulae (1) to (6). The amount of such monomer(s) is not limited, and can range from, e.g., 0.005-5 wt. %, including both more and less than these endpoints, and all amounts in-between this exemplary range. The amount of residual fluorinated monomer can be determined by gas chromatography (GC) or by liquid chromatography (LC), as described in the examples below. The DPS according to the present invention comprises preferably more than 0.005 wt. %, more preferably more than 0.05 wt. %, still more preferably more than 0.5 wt. % and the most preferably more than 1 wt. % of such monomers. On the other hand, it comprises preferably less than 5 wt. %, more preferably less than 4.5 wt. %, still more preferably less than 4 wt. % and the most preferably less than 3.5 wt. %.

In a preferred embodiment herein, the DPS of the invention, meeting at least one impurity limit (maximum allowable content/Purity Standard) set forth above, comprises therein at least one oligo(aryl ether ketone), such as those described in formulaes (7) to (11). The oligo(aryl ether ketone)s can be detected by LC as described in the examples. The amount of such oligo(aryl ether ketone)s is not limited, and can range for example from 0.03 area % to 3 area %, as measured in the examples. Preferably the amount of oligo(aryl ether ketone)s is higher than 0.03 area %, more preferably higher than 0.1 area %, still more preferably higher than 0.5 area % and the most preferably higher than 1.0 area %. On the other hand, the amount of oligo(aryl ether ketone)s is preferably lower than 5 area %, more preferably lower than 4 area %, still more preferably lower than 3 area % and the most preferably lower than 2 area %.

Another aspect of the present invention is related to a method for the preparation of a poly(aryl ether ketone) in a solvent comprising the above described DPS according to the present invention. A related aspect of the present invention concerns the use of the above highly pure DPS in a method for the manufacture of a PAEK.

PAEK can be prepared from a variety of starting materials, either via a nucleophilic route or an electrophilic route. One well known in the art nucleophilic method comprises reacting a generally substantially equimolar mixture of at least one bisphenol and at least one dihalobenzoid compound (for the two-monomer route) or at least one halophenol compound (for the one-monomer route). This nucleophilic route is generally carried out in DPS in the presence of alkali-metal carbonate, often under an inert atmosphere and often at temperatures approaching the melting point of the polymer. The alkali-metal carbonate includes preferably particulate sodium carbonate having a certain particle size distribution, as specified in embodiment (E) hereinafter.

Embodiment (E)

In a preferred embodiment (E) of the present invention, the method for the preparation of a poly(aryletherketone) is a method by aromatic nucleophilic substitution:

in a solvent comprising a diphenyl sulfone, wherein said diphenyl sulfone meets at least one of the above specified impurity limitations, and in the presence of particulate sodium carbonate, wherein said particulate sodium carbonate has a particle size distribution as follows:

$D_{90} \geq 45$ μm and $D_{90} \leq 250$ μm and $D_{99.5} \leq 710$ μm.

As used herein, a sodium carbonate particle size distribution expressed as $D_{xx} \leq Y$ μm refers to the percentage (xx %) of sodium carbonate particles by weight in a sample that are less than or equal to Y μm in diameter.

On one hand, in accordance with embodiment (E), $Na_2CO_3$ that is "too fine" is avoided as it can notably lead to a low bulk density product that is difficult to handle and synthesis reaction kinetics that are difficult to control. With this regard, the Applicant found that $Na_2CO_3$ with a $D_{90} \geq 45$ μm was beneficial.

On the other hand, in accordance with embodiment (E), $Na_2CO_3$ that contains a certain amount of "big" particles, and especially of "very big" particles (i.e., typically of about 710 μm or more), is also to be avoided as it can notably slow down the polymerization rate, or require the use of an undesirably high amount of $K_2CO_3$ or other higher alkali metal carbonate (at fixed $Na_2CO_3$ amount); $Na_2CO_3$ that contains a certain amount of "big" particles, and especially of "very big" particles, can also result in polymerizations having poor kinetics consistency. With this regard, the Applicant found that $Na_2CO_3$ with a $D_{90} \leq 25$ μm and with a $D_{99.5} \leq 710$ μm was also beneficial.

The use of particulate sodium carbonate in accordance with embodiment (E) provides several benefits, including the ability to synthesize easily PAEKs in the absence of a cosolvent forming an azeotrope with water such as p-xylene, and thereby prepare PAEKs with no trace of residual cosolvent (such cosolvents, like p-xylene, are generally toxic). Cosolvents forming an azeotrope with water used in the synthesis of PAEK resins are known to those of skill in the art, and in addition to p-xylene include chlorobenzene, toluene, etc. The use of particulate sodium carbonate in accordance with embodiment (E) makes it also possible to manufacture lower color, whiter PAEK resins. The use of particulate sodium carbonate in accordance with embodiment (E) results also beneficially in improved kinetics consistency.

Preferably, the $D_{99.5}$ of the sodium carbonate particles in accordance with embodiment (E) is of at most 630 μm; more preferably, it is of at most 500 μm; still more preferably, it is of at most 425 μm; most preferably, it is of at most 355 μm.

Preferably, the $D_{90}$ of the sodium carbonate particles in accordance with embodiment (E) is of at least 63 μm; more preferably, it is of at least 90 μm; still more preferably, it is of at least 112 μm.

Preferably, the $D_{90}$ of the sodium carbonate particles in accordance with embodiment (E) is of at most 212 μm; more preferably, it is of at most 180 μm; still more preferably, it is of at most 150 μm.

In certain preferred sub-embodiments of embodiment (E), the sodium carbonate has the following particle size distributions:

$D_{99.5} \leq 630$ $D_{90} \leq 212$ and $D_{90} \geq 45$ μm; or
$D_{99.5} \leq 500$ $D_{90} \leq 212$ and $D_{90} \geq 45$ μm; or
$D_{99.5} \leq 425$ $D_{90} \leq 212$ and $D_{90} \geq 45$ μm; or
$D_{99.5} \leq 630$ $D_{90} \leq 180$ and $D_{90} \geq 45$ μm; or
$D_{99.5} \leq 500$ $D_{90} \leq 180$ and $D_{90} \geq 45$ μm; or
$D_{99.5} \leq 425$ $D_{90} \leq 180$ and $D_{90} \geq 45$ μm; or
$D_{99.5} \leq 630$ $D_{90} \leq 212$ and $D_{90} \geq 63$ μm; or
$D_{99.5} \leq 500$ $D_{90} \leq 212$ and $D_{90} \geq 63$ μm; or
$D_{99.5} \leq 425$ $D_{90} \leq 212$ and $D_{90} \geq 63$ μm; or
$D_{99.5} \leq 630$ $D_{90} \leq 212$ and $D_{90} \geq 90$ μm; or
$D_{99.5} \leq 500$ $D_{90} \leq 212$ and $D_{90} \geq 90$ μm; or
$D_{99.5} \leq 425$ $D_{90} \leq 212$ and $D_{90} \geq 90$ The particle size distribution of the sodium carbonate in accordance with embodiment (E) can be determined by mechanical sieving. This method is appreciated because of its easiness, broad availability, and excellent repeatability. Mechanical sieving is generally based on the mechanical separation of the various fractions on a series of superimposed sieves. The analysis can be made partly or fully in accordance with ASTM E 359-00 (reapproved 2005)$^{\epsilon 1}$, the whole content of which being herein incorporated by reference. ASTM E 359-00 (reapproved 2005)$^{\epsilon 1}$ concerns various measurements made specifically on sodium carbonate, notably sieve analysis. The particle size distribution is advantageously determined with an automatic mechanical sieving device, such as Ro-Tap RX-29 sieve shaker (as commercialized by W. S. Tyler Company). The sieves mounted on the sieve shaker are advantageously in conformity with standard ISO 3310-1 or ASTM E-11, preferably with wire stainless steel circular sieves with square meshes, metal mounting with a diameter 200 mm. The device and its sieves are advantageously checked periodically using a reference powder; the control frequency should be desirably be as high as possible for early detection of any deviation, as possibly resulting for damaged meshes. Typically, it is proceeded as follows: the sieves are superimposed and assembled from top to bottom by descending order of opening mesh; a fixed weight amount of the powder to be investigated is weighed with an analytical balance and placed on top of the widest sieve; by vibrating the sieving machine, the powder material is conveyed through the various sieves; the sieving operation is run for a fixed amount of time; the residues on the sieves are weighed with an analytical balance and related mathematically to the initial weight of material. Notably $D_{90}$ and $D_{99.5}$ values can be calculated from the residues weights. This calculation is generally made as follows:

1) Calculate the weight percentage of the test specimen retained on each sieve

2) Express the weight percentage passing through each sieve, and cumulated

The results can be displayed on a graph were the Y-coordinate represents the cumulative weight percent particles retained on a particular sieve. The X-coordinate corresponds to sieve size. The Y-value for a particular sieve can be determined by adding the weight of the particles retained on that sieve plus the weights of the particles retained on all larger sieves above it and dividing the sum by the total weight of the sample.

The sieves can be ISO 3310-1 or ASTM E-11 test sieves having a diameter of 200 mm, notably commercialized from LAVAL LAB Inc. A certain suitable set of sieves is composed of eight ISO 3310-1 or ASTM E-11 test sieves having a diameter of 200 mm, having the following aperture size or ASTM opening designation: 1000 μm (ASTM No. 18), 500 μm (ASTM No. 35), 250 μm (ASTM No. 60), 180 μm (ASTM No. 80), 125 μm (ASTM No. 120), 90 μm (ASTM No. 170), 63 μm (ASTM No. 230) and 45 μm (ASTM No. 325).

At the end of the sieving analysis, the weight fraction caught on each screen can be calculated. $\Phi_i$, the fraction on sieve i, of size $x_i$, is thus:

$$\phi_i = \frac{w_i}{\sum_{i=1}^{n} w_i}$$

wherein $w_i$ is the weight of powder collected on sieve i sample weight

The percentage under the size $x_t$, $P_t$ is thus defined as:

$$P_t = \sum_{i=1}^{t-1} \phi_i$$

To obtain the cumulative curve, $P_t$, the percentage under the size $x_t$ can be plotted versus $x_t$. The curve can be built by considering in each point the following slope:

$$\left(\frac{dP}{dx}\right)_{x=x_t} = \frac{\phi_t}{x_{t+1} - x_t}$$

3) Determine $D_z$ values (0<z<100), e.g. determine $D_{90}$ and $D_{99.5}$ $D_z$ is defined as the abscissa of the curve for P=z/100, i.e. z wt. % of the sample is under the size of $D_z$.

$D_{90}$ is defined as the abscissa of the curve for P=0.90, i.e. 90 wt. % of the sample is under the size of $D_{90}$.

$D_{99.5}$ is defined as the abscissa of the curve for P=0.995, i.e. 99.5 wt. % of the sample is under the size of $D_{99.5}$.

Exemplary Method for Measuring the Particle Size Distribution, in Particular the $D_{90}$ and $D_{99.5}$, of Particulate $Na_2CO_3$ Apparatus:
 Mechanical sieving apparatus able to transmit combined movements in the horizontal plane and shocks along the vertical axis to a pile of superimposed sieves (apparatus used: RO-TAP RX-29 Model or equivalent, with 278 horizontal revolutions and 150 taps per minute)
 Series of circular sieves, wire stainless steel with square meshes, metal mounting with a diameter 200 mm, in conformity with NF ISO 3310-1 standard and periodically checked using a reference powder.
 Sieves superimposed by descending order of opening mesh (size in μm): 1000 μm, 500 μm, 250 μm, 180 μm, 125 μm, 90 μm, 63 μm and 45 μm.
 Analytical balance, accuracy 0.01 g.

Method:
 Test Specimen: 70 g of powder weighed to 0.01 g.
 Transfer the test specimen on the pile of sieves and position it in the apparatus
 Sieve for 15 minutes.
 Weigh the content of each sieve to 0.01 g.

Calculation:
 Calculate the weight percentage of the test specimen retained on each sieve.
 Express the weight percentage passing through each sieve, and cumulated.
 Determine by graphical interpolation the mesh opening equivalent to the 90% and 99.5% cumulated weight percentage ($D_{90}$, $D_{99.5}$).

The particle size distribution of the sodium carbonate used in accordance with embodiment (E) is advantageously determined on a sample which is representative of the whole sodium carbonate which is used in said process. To achieve appropriate sampling, the skilled person will advantageously rely upon all those sampling recommendations which do form part of the general knowledge and are broadly described in various encyclopedias, including but not limited to "Sampling", Reg. Davies, in "Kirk-Othmer Encyclopedia of Chemical Technology", online Ed. 2000, the whole content of which is herein is incorporated by reference. Since sodium carbonate can be viewed as a free-flowing powder, sampling procedures suitable for stored free-flowing powders will be used preferably.

Sodium carbonate is broadly commercially available, either in the form of dense sodium carbonate or light sodium carbonate. Light sodium carbonate, also called light soda ash, has generally a free flowing density, as measured in accordance with ISO 903 standard, of between 0.48 kg/dm³ and 0.65 kg/dm³. Dense sodium carbonate, commonly called dense soda ash, has generally a free flowing density, as measured in accordance with ISO 903 standard, of from 0.90 kg/dm³ to 1.20 kg/dm³. In general, neither the commercially available dense sodium carbonates nor the commercially available light sodium carbonates have a particle size distribution as required by embodiment (E). Yet, as will explained below, it is easy for the skilled person, searching for obtaining a sodium carbonate with the appropriate particle size requirements, to obtain it.

Dense sodium carbonates having the particle size distribution as required by present embodiment (E) can be notably obtained by appropriate grinding and/or sieving dense sodium carbonates having a particle size distribution not in accordance with embodiment (E). Insofar as dense sodium carbonates are concerned, methods including at least one grinding step followed by at least one sieving step are preferred. As suitable grinders, it can be notably cited jet mills such as helical jet mills, oval tube jet mills, counterjet mills, fluidized bed jet mills, and ball and plate jet mills, can notably be used. As suitable sieves, it can be notably cited 710 μm, 630 μm, 500 μm, 400 μm, 300 μm, 250 μm, 200 μm, 150 μm and 125 μm sieves.

Light sodium carbonates having the particle size distribution as required in present embodiment (E) can also be obtained by appropriate grinding and/or sieving light sodium carbonates having a particle size distribution not in accordance with embodiment (E). However, insofar as light sodium carbonates are concerned, methods free of any grinding step are preferred; such methods may include a sieving step or not. A particularly preferred method for obtaining light sodium carbonates having the particle size distribution in accordance with embodiment (E) comprises selecting said light sodium carbonates among different lots of one or more grades of commercially available light sodium carbonates, as detailed below. The Applicant determined the particle size distribution of numerous lots of commercially available (unground) light sodium carbonates from different sources, and observed that, among all these lots, none had a $D_{90}$ below 45 μm; as a matter of fact, their $D_{90}$ often ranged usually from about 100 μm to about 250 μm, i.e. the lots often complied with both requirements set forth for the $D_{90}$ in accordance with embodiment (E) of the present invention. Concerning the $D_{99.5}$ of the commercially available light sodium carbonates, the Applicant observed surprisingly that its variability from one lot to another was very high, including when considering lots produced at relatively short intervals of time by the same manufacturer in the same plant; it deduced wisely therefrom that this variability could be exploited to its own benefit, because, among the lots produced, certain had the appropriate particle size requirements, while certain other lots of the same commercial grade had a $D_{99.5}$ above 710 μm, not in accordance with embodiment (E) of the present invention. Among the tested sodium carbonates, SODASOLVAY® L sodium carbonate, as produced notably in Dombasle or Rosignano plants, is particularly attractive because a rather high fraction of this commercial grade is formed by lots in accordance with the invention; thus, the Applicant could very easily identify appropriate lots suitable for use in accordance with embodiment (E) of the present invention.

An important and surprising benefit resulting from the use of sodium carbonate powder meeting the requirements of embodiment (E) is that it allows one to limit the amount of potassium carbonate, and more generally of any other higher alkali metal carbonate, to be used in the preparation of the PAEK. As higher alkali metal carbonates other than potassium carbonate, it can be particularly cited rubidium carbonate and caesium carbonate.

Thus, in accordance with embodiment (E), the molar ratio of A/Na (wherein A designates either K, Cs or Rb or any combination thereof) can be of at most 0.050 mol A/mol Na, preferably at most 0.020 mol A/mol Na, and more preferably at most 0.010 mol A/mol Na. In an especially surprising particular sub-embodiment, the molar ratio of A/Na is equal to 0 (i.e. the nucleophilic substitution takes place in the absence of K, Cs and Rb). In another sub-embodiment, the molar ratio of A/Na, although being maintained at a low level (e.g. in accordance with the above specified upper limits), is above 0, preferably of at least 0.001 mol A/mol Na, more preferably of at least 0.002 mol A/mol Na and still more preferably of at least 0.003 mol A/mol Na.

Unlike the particle size distribution of the sodium carbonate, the particle size distribution of the potassium carbonate, when present, is not important, although a slight additional improvement in terms of polymerization kinetics might be observed when using a very finely ground potassium carbonate. Still another aspect of the present invention is related to a PAEK obtainable by the above described method.

In a particular sub-embodiment of embodiment (E), the method for the preparation of a poly(aryletherketone) meets further the technical limitations as met in accordance with previously described embodiment (D).

The PAEK is preferably PEK or PEEK.

The above written description of the invention provides a manner and process of making and using it such that any person skilled in this art is enabled to make and use the same, this enablement being provided in particular for the subject matter of the appended claims, which make up a part of the original description and including the following preferred embodiments:

As used herein, the phrases "selected from the group consisting of" "chosen from" and the like include mixtures of the specified materials. Terms such as "contain(s)" and the like as used herein are open terms meaning "including at least" unless otherwise specifically noted. Phrases such as "mention may be made" etc. preface examples of materials that can be used and do not limit the invention to the specific materials, etc., listed.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

EXAMPLES

As noted above, those of ordinary skill in the art know how to measure, and are capable of measuring, the amount of the impurities noted above that are present in DPS to determine whether the invention maximum allowable content of a given impurity is met. However, where there is a conflict in measurement methods, the following methods control.

Analysis of Acidity or Basicity in Diphenyl Sulfone

Approximately 3 g of diphenyl sulfone sample was weighed to the nearest 0.1 mg and added to an empty glass titration vessel. 55 ml of high-purity methylene chloride was added, followed by addition of a 5.00 ml aliquot of spiking solution, which contains six drops of 37% hydrochloric acid per liter, into the same titration vessel. The vessel was then attached to the titrator cell assembly containing the buret tip, pH electrode, and magnetic stirrer. The vessel was then purged with carbon dioxide-free nitrogen for 5-7 minutes. While continuing the nitrogen purge, the vessel contents were titrated with 0.025 N tetrabutylammonium hydroxide in 1:12 methanol:toluene and the volume of titrant required to reach the strong acid endpoint was measured. A blank titration was performed using the same parameters, except that the sample was omitted. Results were calculated using the following equation:

$$\text{Acidity} = ((VS1-VB1)*N*100000)/W \text{ in microequivalents per gram of sample}$$

Where VS1 is the amount of titrant in ml required to reach the strong acid/base equivalence points when sample solution is titrated and VB1 is the amount of titrant in ml required to reach the strong acid/base equivalence point when only the blank solution is titrated, W is the sample weight, and N is the normality of the tetrabutylammonium hydroxide titrant. If acidity is negative, the sample contains basic species.

Determination of Sodium, Potassium, and Iron in Diphenyl Sulfone

Concentrations of sodium, potassium, and iron were measured in diphenylsulfone by ashing of the sample followed by measurement of element concentration by inductively-coupled plasma atomic emission spectrometry. Approximately 3 g of diphenylsulfone sample was weighed into platinum crucibles using an analytical balance. Two drops of concentrated, trace metals grade sulfuric acid was added to each sample and the crucibles were placed into a muffle furnace set to 250° C. After the diphenylsulfone has vaporized, the furnace temperature was raised to 525° C. for 1 hour to remove any organic residues. Metallic residues were dissolved by adding 1 ml of concentrated hydrochloric acid to the crucible and warming at 50° C. to dissolve the ash. After addition of 5 ml of deionized water and additional warming, crucible contents were quantitatively transferred to a 25-ml volumetric flask, diluted to the mark with deionized water, and mixed well. The diluted solutions were then analyzed by ICP-AES against standards made from certified sodium, potassium, and iron standard solutions. Emission was monitored at the following wavelengths for the elements of interest: sodium: 589.592 nm, potassium: 766.490 nm and iron: 238.204 nm. Plasma conditions used for the analysis were:

plasma input power: 1300 watts, plasma argon flow: 15 liters per minute, auxiliary argon flow: 0.5 liters per minute, nebulizer flow: 1.2 liters per minute, and sample flow rate: 1.5 milliliters per minute. Element concentrations in the samples were calculated by the ICP operating software from the element emission line intensities.

Determination of Total Chlorine in Diphenyl Sulfone

Using forceps, a clean, dry combustion boat was placed onto a microbalance, and the balance was zeroed. 1 mg of diphenylsulfone sample was weighed into the boat and weight was recorded to 0.001 mg. The combustion boat and sample were placed in the introduction port of a Thermo Electron Corporation ECS 1200 Halogen Analyzer, and the port was capped. The sample weight was entered into the sample weight field on the instrument computer. The sample analysis cycle was then started. The sample was burned in a mixture of argon and oxygen and the combustion products were carried by the combustion gas stream into a titration cell. Hydrogen chloride produced from the combustion was absorbed into the cell solution from the gas stream, and was coulometrically titrated with silver ions. Total chlorine content was displayed at the end of the titration.

Determination of Water in Diphenyl Sulfone

Water content in diphenyl sulfone was determined according to ASTM D6869-03 (Karl Fisher), with the following parameters:
Purge oven temperature: 100° C.
Purge time: 1800 seconds
Sample weight: 1 g weighed to 0.0001 g
Calibration: pure water (micro-capillary method in this method)
Carrier gas: argon dried with molecular sieve 4A
Carrier gas flow rate: 100 ml/min.

The water in the vapors was analyzed by Karl Fisher volumetric titration.

Determination of the Concentration of Diphenylsulfide, Residual Fluorinated Monomer and Oligo(Aryl Ether Ketone)s in Diphenylsulfone by Liquid Chromatography HPLC analysis was carried out on a Waters Alliance 2795 LC instrument using a Supelco Discovery HS F5 25 cm×4.6 mm column. The analysis conditions were:
Mobile phase: acetonitrile/deionized water.
Gradient: 60/40 acetonitrile/water, hold for 5 minutes, increase to 100% acetonitrile in further 10 minutes, hold for 5 minutes at 100% acetonitrile
Flow rate: 1 ml/minute
Injection volume: 10 μl
Detection: UV at 254 nm The sample was prepared by dissolving 0.2 g of DPS in 10 g of acetonitrile. The concentration of diphenyl sulfide and of residual monomer was determined using a low concentration diphenyl sulfide and monomer standards as an external calibration standards (commercially available). The retention time for DPS was 6.2 minutes and the retention time for diphenyl sulfide was 10.7 minutes. The retention time for 4,4'-difluorobenzophenone was 9.1 minutes. The retention times of oligo(aryl ether ketone)s such as those depicted in formulaes (7), (8) and (11) are 15.3, 18.0 and 15.1, minutes. They were identified by LC-MS (liquid chromatography coupled with mass spectrometry). Their concentration in the DPS sample was assessed by the area of these peaks/total peak area of DPS plus impurities.

Determination of Monochlorodiphenylsulfones and Monomethyldiphenylsulfones in Diphenyl Sulfone by Gas Chromatography GC analysis was performed on an HP5890 series 11 gas chromatograph using a Restek RTx-5MS, 15 m×0.25 mm internal diameter×0.25 μm film thickness column. The following GC conditions were used:
Helium flow rate: 1 ml/minute,
Injector temperature: 250° C.
FID temperature: 250° C.
Oven Temperature Program: 100° C., hold 1 minute, 30° C./minute to 250° C., hold 1 minute
Total run time: 14 minutes
Injection volume: 1 μl
Split 40:1

The sample was prepared by dissolving 0.2 g of DPS in 5 ml of acetone. The GC retention times for monomethyl diphenylsulfone isomers were 8.0 and 8.1 minutes and for monochlorodiphenylsulfone 8.2 minutes. The identity of the impurities was determined by GCMS run on the sample solution. The impurity concentrations were quoted as area %, calculated from GC FID peak areas. When several isomers were present, the concentration includes the sum of these isomers.

Determination of Color (APHA) of DPS in Acetone 20 g of diphenyl sulfone are dissolved in 80 g of acetone at 25° C. The acetone used contains less than 0.5 wt. % water.

Color of the solution is measured as compared to Pt—Co standards in the APHA scale (ASTM D1209-00), using a Gretag Macbeth Color Eye Ci5 Spectrophotometer for the comparison.

The blank used was distilled water.

Color Measurement of Final Polymer

The color of a molded plaque (2.5 mm thick obtained by compression molding at 370° C./19.4 bar/15 minutes then 370° C./26.1 bar/5 minutes. To ensure full crystallization, the plaque was slowly cooled down to room temperature over 40 minutes) was measured under D65 light source at 10° angle (1964 CIE). Color measurements are expressed with L*, a*, b* tristimulus coordinates defined by the CIE (Commission Internationale de l'Eclairage) in 1976 (K. Nassau, in "Kirk-Othmer Encyclopedia of Chemical Technology", 2004, Chapter 7, P 303-341). All measurements were made on Gretag Macbeth Color Eye Ci5 Spectrophotometer, with tribeam diffuse/8" 6" sphere optical geometry, a bandpass of 10 nm, a spectral range of 360 nm to 750 nm. Plaques were measured directly on the spectrometer eye and only one reading was taken. The illuminant was D65 (natural daylight). L*, a*, b* were measured according to ASTM E308-06. No bandpass correction was applied.

Intrinsic Viscosity

Intrinsic viscosities were measured at 30° C. in anhydrous methane sulfonic acid using a Cannon-Fenske viscometer tube (No. 50). The average of inherent viscosities and reduced viscosities extrapolated to zero concentrations was used.

Reaction Examples 1 Through 11

Diphenyl sulfone used in these examples was supplied by different companies: Proviron (Belgium), Sloss (US), Wuhan Zhengmao (China) and used without further purification. The analysis of these samples was carried out per the analysis methods described.

In a 500 ml 4-neck reaction flask fitted with a stirrer, a $N_2$ inlet tube, a Claisen adapter with a thermocouple plunging in the reaction medium, and a Dean-Stark trap with a condenser and a dry ice trap were introduced 127.82 g of diphenyl sulfone of quality defined hereafter in table 1, 28.5983 g of p-hydroquinone (p-hydroquinone can typically contain up to 0.6% water—the weight here is the weight of p-hydroquinone on a dry basis, i.e. after correction for the moisture content), and 57.2337 g of 4,4'-difluorobenzophenone (containing 2,4'- difluorobenzophenone and 4-monofluorobenzophenone in a cumulated amount of at most 1250 ppm).

Reaction examples 3 and 4 were run under more dilute conditions, with 175.00 g of diphenyl sulfone, instead of 127.82 g. The flask content was evacuated under vacuum and then filled with high purity nitrogen (containing less than 10 ppm $O_2$). The operation was repeated twice. The reaction mixture was then placed under a constant nitrogen purge (60 ml/min).

The reaction mixture was heated slowly to 150° C. At 150° C., a mixture of 28.4259 g of dry $Na_2CO_3$ having a $D_{90} \geq 45$ µm, a $D_{90} \leq 250$ µm and a $D_{99.5} \leq 710$ µm; and 0.1800 g of dry, very finely ground $K_2CO_3$ ($D_{90}$<45 µm) was added via a powder dispenser to the reaction mixture over 30 minutes. At the end of the addition, the reaction mixture was heated to 320° C. at 1° C./minute. After 50 minutes at 320° C., 6.8203 g of 4,4'-difluorobenzophenone (containing 2,4'-difluorobenzophenone and 4-monofluorobenzophenone in a cumulated amount of at most 1250 ppm) were added to the reaction mixture while keeping a nitrogen purge on the reactor. After 5 minutes, 0.4420 g of lithium chloride were added to the reaction mixture. 10 minutes later, another 2.2734 g of 4,4'-difluorobenzophenone (containing 2,4'-difluorobenzophenone and 4-monofluorobenzophenone in a cumulated amount of at most 1250 ppm) were added to the reactor and the reaction mixture was kept at temperature for 15 minutes. The reactor content was then poured from the reactor into a SS pan and cooled. The solid was broken up and ground in an attrition mill through a 2 mm screen. Diphenyl sulfone and salts were extracted from the mixture with acetone and water at pH between 1 and 12. The last wash water had a pH between 6 and 7. The powder was then removed from the reactor and dried at 120° C. under vacuum for 12 hours yielding 67-70 g of a white powder.

Examples 1 through 5 describe the use of high purity DPS in the preparation of high quality PEEK.

Examples 6 through 11 are comparative examples showing the adverse effect of:
High sodium and chlorine contents (6 and 7)
High iron content (7)
High residual acidity (8)
High monomethyldiphenylsulfone (9)
High monochlorodiphenylsulfone and chlorine contents (10)
High water content (11).

Example 12

Recovery of Diphenyl Sulfone by Distillation in Glassware and its Use in PEEK Reaction A mixture containing 81.1 wt. % acetone, 12.2 wt. % diphenyl sulfone water, 6.1 wt. % water, 0.51 wt. % 4,4'-difluorobenzophenone (monomer), 650 ppm NaCl and 60 ppm KCl, was produced by extracting 1300 g of reaction mixture from example 1 with 5140 g of acetone containing 7 wt. % water. The extract also contains an undetermined amount of p-hydroquinone salt, oligo(aryl ether ketone)s, etc.

In a 10 l glass 4-neck round-bottom flask, fitted with a mechanical stirrer (made of glass), a thermocouple in glass thermowell, a nitrogen inlet tube, an insulated Vigreux column with a collection flask, was introduced 4.9 kg of the above-described solution. Under atmospheric pressure, acetone was collected between 55 and 63° C. (liquid temperature). Then pressure was increased to 2.7 bar with nitrogen and the temperature increased to 130° C. Water was collected overhead. The pressure was then decreased to 76 Torr and the still temperature was increased to 250-255° C. A mixture of 4,4'-difluorobenzophenone and diphenyl sulfone was collected overhead. The pressure was further reduced to 52 Torr and, at the same temperature, the remaining diphenyl sulfone was collected overhead. The final mixture of diphenyl sulfone and 4,4'-difluorobenzophenone (0.57 wt. %) was recovered with a 85% yield (251 g isolated). The analysis results of the diphenyl sulfone thus obtained can be found in entry 12 in Table 1.

The recovered solvent (DPS) was used to prepare PEEK as follows:

In a 500 ml 4-neck reaction flask fitted with a stirrer, a $N_2$ inlet tube, a Claisen adapter with a thermocouple plunging in the reaction medium, and a Dean-Stark trap with a condenser and a dry ice trap were introduced 128.55 g of recovered diphenyl sulfone of quality defined hereafter in table 1, 28.5983 g of p-hydroquinone (p-hydroquinone can typically contain up to 0.6% water—the weight here is the weight of p-hydroquinone on a dry basis, i.e. after correction for the moisture content) and 56.5009 g of 4,4'-difluorobenzophenone (containing 2,4'-difluorobenzophenone and 4-monofluorobenzophenone in a cumulated amount of at most 1250 ppm). The flask content was evacuated under vacuum and then filled with high purity nitrogen (containing less than 10 ppm $O_2$). The operation was repeated twice. The reaction mixture was then placed under a constant nitrogen purge (60 ml/min).

The reaction mixture was heated slowly to 150° C. At 150° C., a mixture of 28.4259 g of dry $Na_2CO_3$ having a $D_{90} \geq 45$ µm, a $D_{90} \leq 250$ µm and a $D_{99.5} \leq 710$ µm and 0.1800 g of dry, very finely ground $K_2CO_3$ ($D_{90}$<45 µm) was added via a powder dispenser to the reaction mixture over 30 minutes. At the end of the addition, the reaction mixture was heated to 320° C. at 1° C./minute. After 50 minutes at 320° C., 6.8203 g of 4,4'-difluorobenzophenone (containing 2,4'-difluorobenzophenone and 4-monofluorobenzophenone in a cumulated amount of at most 1250 ppm) were added to the reaction mixture while keeping a nitrogen purge on the reactor. After 5 minutes, 0.4420 g of lithium chloride were added to the reaction mixture. 10 minutes later, another 2.2734 g of 4,4'-difluorobenzophenone (containing 2,4'-difluorobenzophenone and 4-monofluorobenzophenone in a cumulated amount of at most 1250 ppm) were added to the reactor and the reaction mixture was kept at temperature for 15 minutes. The reactor content was then poured from the reactor into a SS pan and cooled. The solid was broken up and ground in an attrition mill through a 2 mm screen. Diphenyl sulfone and salts were extracted from the mixture with acetone and water at pH between 1 and 12. The last wash water had a pH between 6 and 7. The powder was then removed from the reactor and dried at 120° C. under vacuum for 12 hours yielding 66.54 g of a white powder.

Example 13

Recovery of Diphenyl Sulfone by Precipitation with a Non Solvent

The same extract as used in example 12 was used: mixture containing 81.1 wt. % acetone, 12.2 wt. % diphenyl sulfone, 6.1 wt. % water, 0.51 wt. % 4,4'-difluorobenzophenone, 650 ppm NaCl and 60 ppm KCl.

In a 5000 ml 2-neck-round-bottom flask, fitted with a mechanical stirrer, were introduced 2000 g of deionized water. Under vigorous mechanical agitation, 1000 g of the above-mentioned extract were added to the flask. The slurry was kept under agitation at room temperature for 15 minutes. The solid was then isolated by filtration on a Buchner funnel.

The concentration of diphenyl sulfone in the liquid was 0.13 wt. %. The solid was reintroduced on the flask and 2000 g deionized were added. The slurry was agitated at room temperature for 30 minutes. The solid was then isolated by filtration on a Buchner funnel. The wet cake (159.8 g) was dried under vacuum (100 Torr) at 60° C. overnight. The analysis of recovered diphenyl sulfone (114.5 g, 91% yield) is found in entry 13 of the Table 1.

The DPS thus obtained was used in a polymerization reaction similar to example 11, except that the amounts of recovered diphenyl sulfone used was 131.77 g and the amount of virgin 4,4'-difluorobenzophenone used was 53.2805 g. Results can be found in entry 13, table 1.

Example 14

Recovery of Diphenyl Sulfone by Precipitation with a Non Solvent, then Evaporation of a Fraction of the Low Boiling Solvent A mixture containing 81.1 wt. % acetone, 12.2 wt. % diphenyl sulfone, 6.1 wt. % water, 0.51 wt. % 4,4'-difluorobenzophenone, 650 ppm NaCl and 60 ppm KCl was obtained by extraction of a typical polymerization mixture.

In a 5000 ml 2-neck-round-bottom flask, fitted with a mechanical stirrer, were introduced 2000 g of deionized water. Under vigorous mechanical agitation, 2000 g of the above-mentioned extract were added to the flask. A solid precipitate was formed immediately. The reaction flask was then fitted with a distillation overhead and the slurry was heated up to 56-63° C. under agitation. When 923 g acetone had been collected overhead, the setup was switched to total reflux conditions and the slurry was cooled down to room temperature (23° C.). The solid was then isolated by filtration on a Buchner funnel. The concentration of diphenyl sulfone in the liquid was 0.10 wt. %. The solid was reintroduced on the flask and 4000 g deionized were added. The slurry was agitated at room temperature for 30 minutes. The solid was then isolated by filtration on a Buchner funnel. The wet cake (325.4 g) was dried under vacuum (100 Torr) at 70° C. overnight. The analysis of recovered diphenyl sulfone (228.5 g, 90% yield) is found in entry 14 of Table 1.

The DPS thus obtained was used in a polymerization reaction similar to example 11, except that the amounts of recovered diphenyl sulfone used was 131.91 g and the amount of virgin 4,4'-difluorobenzophenone used was 53.1445 g. Results can be found in entry 14, table 1.

Example 15

Recovery of Diphenyl Sulfone by Crystallization

Reaction mixture (1300 g) from example 1 was extracted with xylene (2600 g) at reflux temperature. The extract was then concentrated by evaporation of xylene at atmospheric pressure to generate a typical extract as follows. Only the identified compounds are detailed. As for the other examples, some other compounds like oligo(aryl ether ketone)s were also present.

In a 1000 ml 2 neck-round-bottom flask, fitted with a reflux condenser and a mechanical stirrer, 800 g of refluxing mixture containing 58.3 wt. % p-xylene, 40.0 wt. % diphenyl sulfone and 1.7 wt. % 4,4'-difluorobenzophenone (monomer) were cooled down at 5° C./min to 10° C. under agitation. The solid formed upon cooling (solid started to appear at 80° C.) was isolated by filtration on Buchner. The wet cake (352 g) containing diphenyl sulfone, 4,4'-difluorobenzophenone and xylene (10 wt. %), was reintroduced in the flask with 1056 g of deionized water. A Dean-Stark trap was fitted on top of the round-bottom flask, in replacement of the reflux condenser. The slurry was heated to 92° C. under agitation, and xylene was removed from the slurry as an azeotrope with water. When no more xylene was removed from the refluxing slurry, the mixture was cooled to down temperature and the solid isolated on Buchner funnel. After drying under vacuum (100 Torr)/60° C., 309 g diphenyl sulfone containing 2.72 wt. % 4,4'-difluorobenzophenone was isolated. The analysis of recovered diphenyl sulfone is found in entry 15 of the Table 1.

At 10° C., the yield of diphenyl sulfone can be maximized (solubility of diphenyl sulfone in p-xylene at 10° C. is 0.1 wt. %). In case more impurities need to be removed from the diphenyl sulfone, a higher crystallization temperature can be used: at 23° C., the solubility of diphenyl sulfone in p-xylene is 1.38 wt. %.

The DPS thus obtained was used in a polymerization reaction similar to example 11, except that the amounts of recovered diphenyl sulfone used was 131.39 g and the amount of virgin 4,4'-difluorobenzophenone used was 53.6598 g. Results can be found in entry 15, table 1.

Examples 16 to 19

Use of Diphenyl Sulfone Containing Diphenyl Sulfide

A sample of diphenyl sulfone used in example 5 was spiked with diphenyl sulfide (commercial, 98%, Sigma-Aldrich) in different amounts (0.3 to 0.8 wt. %). Using this diphenyl sulfone, the polymerization reaction was done under the same conditions as example 5. Results are in entries 16 to 19 in Table 1.

Comparative Example 20

Recovery by Distillation in the Presence of 316 Stainless Steel

The same procedure as for example 11 was followed but in an 316 Stainless Steel autoclave fitted with a packed column (non structured 316 Stainless Steel packing). The final mixture of diphenyl sulfone and 4,4'-difluorobenzophenone (0.51 wt. %) was recovered with a 79% yield (229 g isolated). The analysis results of the DPS thus obtained can be found in entry 20 in Table 1. The DPS thus obtained was high in color and in iron content.

The DPS thus obtained was used in a polymerization reaction similar to example 11, except that the amounts of recovered diphenyl sulfone used was 128.48 g and the amount of virgin 4,4'-difluorobenzophenone used was 56.5784 g. Results can be found in entry 20, table 1.

The color of the polymer was adversely affected by the impurities in the recovered DPS.

TABLE 1

| | Diphenyl sulfone analysis | | | | | | | | | |
|---|---|---|---|---|---|---|---|---|---|---|
| | Water (wt %) | [DFBP] (wt %) | Oligo (arylether ketone)s (area %) | [monomethyl DPS] (area %) | [monochloro DPS] (area %) | [Na] (ppm) | [K] (ppm) | [Fe] (ppm) | Residual acidity (μeq/g) | [Diphenyl-sulfide] (wt %) |
| 1 | 0.06 | 0 | 0 | 0.02 | <0.01 | 50 | 1 | 1 | 0.08 | <0.01 |
| 2 | 0.08 | 0 | 0 | 0.02 | 0.02 | 15 | 5 | 3 | 0.50 | <0.01 |
| 3 | 0.08 | 0 | 0 | 0.02 | 0.02 | 15 | 5 | 3 | 1.03 | <0.01 |
| 4 | 0.09 | 0 | 0 | 0.02 | 0.02 | 15 | 5 | 3 | 1.95 | <0.01 |
| 5 | 0.08 | 0 | 0 | 0.02 | 0.02 | 15 | 5 | 3 | 0.18 | <0.01 |
| C6 | 0.07 | 0 | 0 | 0.06 | <0.01 | 428 | 8 | 2 | 0.08 | <0.01 |
| C7 | 0.07 | 0 | 0 | 0.03 | <0.01 | 83 | 2 | 10 | 0.08 | <0.01 |
| C8 | 0.06 | 0 | 0 | 0.02 | 0.02 | 15 | 5 | 3 | 2.43 | <0.01 |
| C9 | 0.08 | 0 | 0 | 0.3 | 0.02 | 5 | <2 | <2 | 0.18 | <0.01 |
| C10 | 0.09 | 0 | 0 | 0.02 | 0.08 | 5 | <2 | <2 | 0.18 | <0.01 |
| C11 | 0.25 | 0 | 0 | 0.02 | 0.02 | 5 | <2 | <2 | 0.05 | <0.01 |
| 12 | 0.02 | 0.57 | 0.03 | 0.02 | <0.01 | <2 | <2 | 0.9 | 0.08 | <0.01 |
| 13 | 0.09 | 3 | 1.49 | <0.01 | 0.02 | 4 | <2 | 0.6 | 0.00 | 0.09 |
| 14 | 0.08 | 3.1 | 1.39 | <0.01 | 0.02 | 5 | <2 | 1.2 | 0.00 | 0.11 |
| 15 | 0.08 | 2.72 | 1.09 | 0.02 | 0.03 | 11 | 2 | 3 | 0.20 | <0.01 |
| 16 | 0.08 | 0 | 0 | 0.02 | 0.02 | 12 | 5 | 3 | 0.18 | 0.80 |
| 17 | 0.08 | 0 | 0 | 0.02 | 0.02 | 12 | 5 | 3 | 0.18 | 0.80 |
| 18 | 0.08 | 0 | 0 | 0.02 | 0.02 | 12 | 5 | 3 | 0.18 | 0.31 |
| 19 | 0.08 | 0 | 0 | 0.02 | 0.02 | 12 | 5 | 3 | 0.18 | 0.36 |
| C20 | 0.02 | 0.51 | 0.04 | 0.02 | <0.01 | 17 | <2 | 9 | 0.15 | <0.01 |

| | APHA | | Polymer analysis | | | | |
|---|---|---|---|---|---|---|---|
| | | | | Molded plaque color | | | |
| | 20 wt % sol in acetone | Total Chlorine (ppm) | Intrinsic viscosity (dL/L) | L* | a* | b* | Min L* (target) (95--17*intv) |
| 1 | 10 | 115 | 1.49 | 70.46 | 0.93 | 7.44 | 69.75 |
| 2 | 10 | 35 | 1.32 | 79.28 | 0.60 | 8.58 | 72.56 |
| 3 | 10 | 35 | 1.35 | 74.62 | 1.33 | 7.11 | 72.13 |
| 4 | 10 | 35 | 1.40 | 71.47 | 1.82 | 8.31 | 71.27 |
| 5 | 10 | 35 | 1.43 | 77.03 | 1.12 | 7.42 | 70.62 |
| C6 | 10 | 840 | 1.50 | 62.75 | 0.98 | 4.25 | 69.53 |
| C7 | 10 | 140 | 1.32 | 69.01 | 1.43 | 8.32 | 72.56 |
| C8 | 10 | 35 | 1.29 | 69.38 | 1.42 | 7.77 | 72.99 |
| C9 | 10 | 35 | 0.49 | 65.38 | 0.90 | 4.94 | 86.59 |
| C10 | 10 | 150 | 0.75 | 60.01 | 0.85 | 3.73 | 82.20 |
| C11 | 17 | 35 | No polymer formed | | | | |
| 12 | 10 | 17 | 1.42 | 79.47 | 1.19 | 8.38 | 70.84 |
| 13 | 15 | 15 | 1.27 | 78.75 | 1.17 | 7.65 | 73.42 |
| 14 | 10 | 20 | 1.24 | 77.41 | 1.64 | 9.46 | 73.85 |
| 15 | 15 | 50 | 1.18 | 76.92 | 1.09 | 6.06 | 74.91 |
| 16 | 10 | 35 | 1.54 | 73.42 | 1.10 | 8.59 | 68.88 |
| 17 | 10 | 35 | 1.63 | 70.97 | 0.94 | 6.84 | 67.35 |
| 18 | 10 | 35 | 1.43 | 75.90 | 1.45 | 8.59 | 70.62 |
| 19 | 10 | 35 | 1.43 | 76.61 | 1.64 | 7.91 | 70.62 |
| C20 | 60 | 37 | 1.32 | 66.91 | 2.75 | 7.73 | 72.56 |

[monochloroDPS] and [monomethylDPS] represent the concentrations of all the isomers detected by GC.

What is claimed:

1. A method for the preparation of a poly(aryletherketone) by aromatic nucleophilic substitution, wherein said aromatic nucleophilic substitution comprises reacting a substantially equimolar mixture of at least one bisphenol and at least one dihalobenzoid compound or at least one halophenol compound in a solvent comprising a diphenyl sulfone wherein said diphenyl sulfone has been used in the preparation of a poly(aryletherketone) (used DPS), and wherein said used DPS meets all of the following impurity limitations:

| | |
|---|---|
| Monomethyldiphenylsulfone content (sum of all isomers) | Less than 0.2 area % |
| Monochlorodiphenylsulfone content (sum of all isomers) | Less than 0.08 area % |
| Sodium content | Less than 55 ppm |
| Potassium content | Less than 15 ppm |
| Iron content | Less than 5 ppm |
| Residual acidity content | Less than 2.0 μeq/g |
| Diphenyl sulfide content | Less than 2.0 wt. % |
| APHA of 20 wt. % solution in acetone at 25° C. | Less than 50 |
| Total chlorine content | Less than 120 ppm | wherein ppm and wt. % are based on the total weight of the used DPS and area % represents the ratio of the GC peak area of the impurity of concern over the total area of all GC peaks of the used DPS.

2. The method according to claim 1, wherein said used DPS further comprises therein more than 0.03 area % of one or more oligo(aryl ether ketone) impurities, wherein area % represents the ratio of the LC peak area of the impurity of concern over the total area of all LC peaks of the used DPS.

3. The method according to claim 2, wherein the oligo(aryl ether ketone) impurities are complying with those of structures (7) to (11), as shown below:
(7)
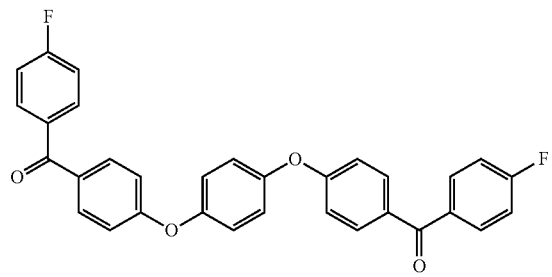
(8)
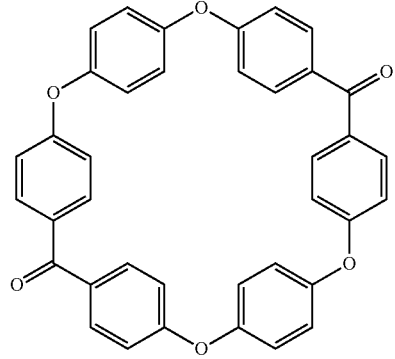
(9)
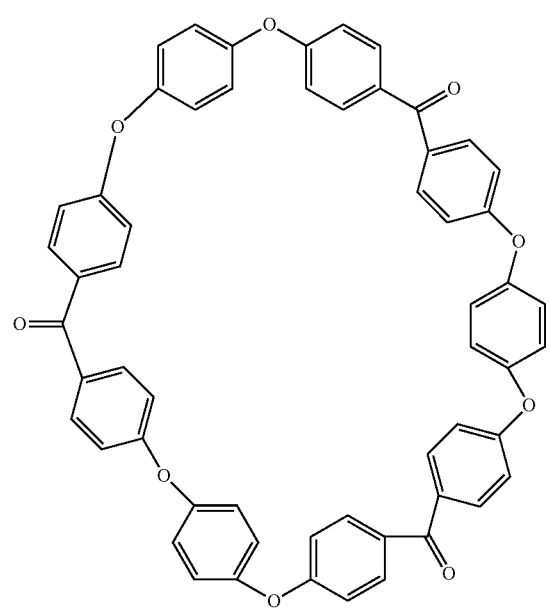
-continued
(10)
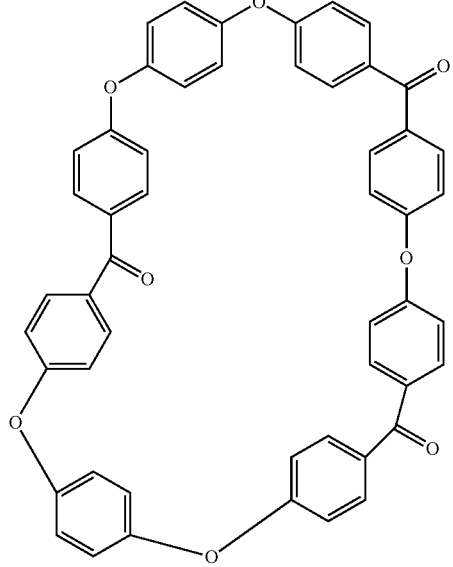
(11)
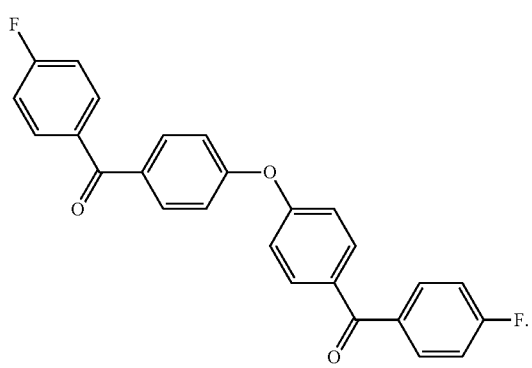
4. The method according to claim 1 wherein said used DPS comprises at least one fluorinated monomer.
5. The method according to claim 4, wherein said fluorinated monomer is selected from the group consisting of:
(1)
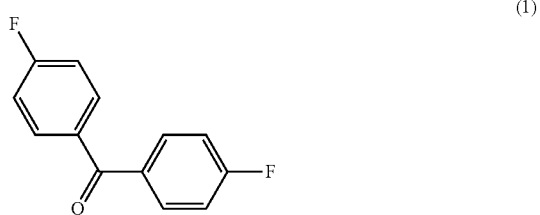

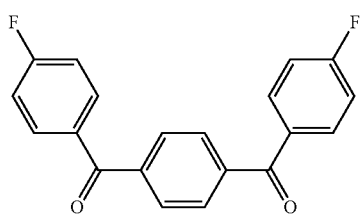
(2)

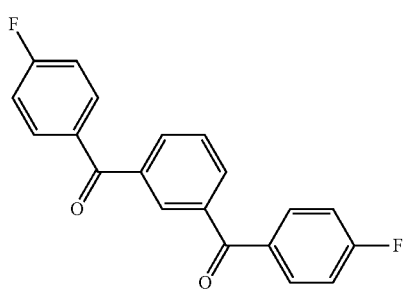
(3)

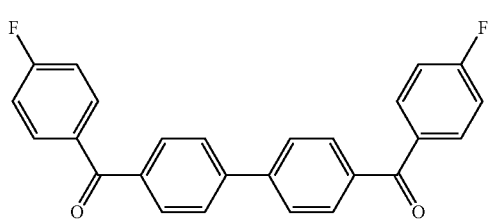
(4)

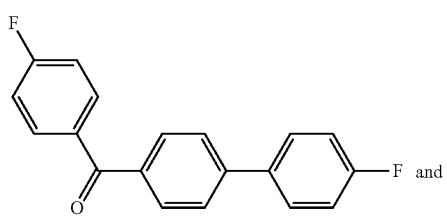
(5)

and

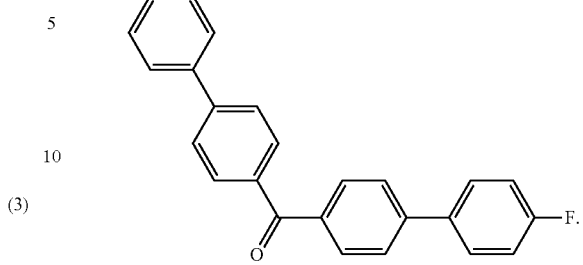
(6)

6. The method according to claim 1, wherein said used DPS further meets the following impurity limitation:
a water content of less than 0.1 wt. %.

7. The method according to claim 1, wherein the poly (aryletherketone) is poly(ether ether ketone).

8. The method according to claim 1, wherein said used DPS is purified by distillation, liquid chromatography, adsorption and/or absorption on silica or other solid media, ion exchange techniques, extraction, (re)crystallization and/or precipitation.

9. The method according to claim 1, which is a method by aromatic nucleophilic substitution in the presence of particulate sodium carbonate, wherein said particulate sodium carbonate has a particle size distribution as follows:
$D_{90} \geq 45$ μm and $D_{90} \leq 250$ μm and $D_{99.5} \leq 710$ μm.

10. The method according to claim 1, which is a method for the preparation of a semi-crystalline poly(aryl ether ketone) by aromatic nucleophilic substitution, wherein a nucleophile is reacted with a 4,4'-difluorobenzophenone, said 4,4'-difluorobenzophenone meeting the following impurity limitation:
[2,4'-difluorobenzophenone]+[4-monofluorobenzophenone]≤1250 ppm,
wherein the amounts of 2,4'-difluorobenzophenone and 4-monofluorobenzophenone in 4,4'-difluorobenzophenone are determined by liquid chromatography analysis.

11. A poly(aryletherketone) obtained by the method according to claim 1, wherein a compression molded plaque of the obtained poly(aryletherketone) has a color L* coordinate of $>90-17*$intrinsic viscosity ($\eta_{int}$), wherein L* is measured according to ASTM E308 using D 65 illuminant at 10° angle and $\eta_{int}$ is measured in methane sulfonic acid at 30° C.

* * * * *